United States Patent
Kim et al.

(10) Patent No.: US 12,190,511 B2
(45) Date of Patent: Jan. 7, 2025

(54) METHOD OF PROVIDING DIAGNOSIS ASSISTANCE INFORMATION AND METHOD OF PERFORMING THE SAME

(71) Applicant: NEUROPHET INC., Seoul (KR)

(72) Inventors: Dong Hyeon Kim, Seoul (KR); Min Ho Lee, Goyang-si (KR)

(73) Assignee: NEUROPHET INC., Seoul (KR)

( * ) Notice: Subject to any disclaimer, the term of this patent is extended or adjusted under 35 U.S.C. 154(b) by 100 days.

(21) Appl. No.: 17/879,727

(22) Filed: Aug. 2, 2022

(65) Prior Publication Data

US 2022/0366565 A1 Nov. 17, 2022

Related U.S. Application Data

(63) Continuation of application No. 17/491,336, filed on Sep. 30, 2021, now Pat. No. 11,449,995, which is a continuation of application No. PCT/KR2020/019458, filed on Dec. 30, 2020.

(51) Int. Cl.
*G06T 7/00* (2017.01)
*G06T 7/11* (2017.01)
*G16H 30/40* (2018.01)
*G16H 70/60* (2018.01)

(52) U.S. Cl.
CPC ............. *G06T 7/0012* (2013.01); *G06T 7/11* (2017.01); *G16H 30/40* (2018.01); *G16H 70/60* (2018.01); *G06T 2207/10088* (2013.01); *G06T 2207/30016* (2013.01)

(58) Field of Classification Search
CPC .............. G06T 7/0012; G06T 7/11; G06T 2207/10088; G06T 2207/30016; G06T 2207/10081; G16H 70/60; G16H 30/40
See application file for complete search history.

(56) References Cited

U.S. PATENT DOCUMENTS

| | | | |
|---|---|---|---|
| 6,430,430 B1* | 8/2002 | Gosche | G06T 7/155 |
| | | | 128/923 |
| 2011/0105881 A1 | 5/2011 | Kakimoto | |
| 2011/0194741 A1 | 8/2011 | Ekin | |
| 2013/0257910 A1 | 10/2013 | Park et al. | |

(Continued)

FOREIGN PATENT DOCUMENTS

| | | |
|---|---|---|
| CN | 108171697 A | 6/2018 |
| KR | 10-2013-0109838 A | 10/2013 |

(Continued)

OTHER PUBLICATIONS

KR Notice of Allowance in Application No. 10-2020-0187938 dated Jun. 3, 2021.

(Continued)

*Primary Examiner* — Winta Gebreslassie
*Assistant Examiner* — Vu Le
(74) *Attorney, Agent, or Firm* — Maschoff Brennan

(57) ABSTRACT

The present invention relates to a method of providing diagnosis assistance information by analyzing a medical image, the method including obtaining an image of the brain, labeling a feature value representing a region of the brain, determining a reference boundary in the image of the brain, calculating a first disease index and a second disease index, and providing diagnosis assistance information on the basis of the first and second disease indexes.

18 Claims, 43 Drawing Sheets

(56) References Cited

U.S. PATENT DOCUMENTS

| | | |
|---|---|---|
| 2016/0110904 A1 | 4/2016 | Jeon et al. |
| 2020/0315455 A1 | 10/2020 | Lee et al. |
| 2021/0257094 A1 | 8/2021 | Takemoto |
| 2021/0343008 A1 | 11/2021 | Okuda |
| 2022/0172370 A1* | 6/2022 | Lee .................. G06T 7/0012 |

FOREIGN PATENT DOCUMENTS

| | | |
|---|---|---|
| KR | 10-2016-0046625 A | 4/2016 |
| KR | 10-1754291 B1 | 7/2017 |

OTHER PUBLICATIONS

KR Notice of Allowance in Application No. 10-2020-0187935 dated Jun. 14, 2021.

Fazekas, F. et al., "MR Signal Abnormalities at 1.5 T in Alzheimer's Dementia and Normal Aging," AJR, vol. 149, pp. 351-356 (Aug. 1987).

Fazekas, F. et al., "Pathologic correlates of incidental MRI white matter signal hyperintensities," Neurology, vol. 43, pp. 1683-1689 (Sep. 1993).

Firbank, M.J. et al., "Brain atrophy and white matter hyperintensity change in older adults and relationship to blood pressure," Journal of Neurology, vol. 254, pp. 713-721 (2007).

Armitage, P.A. et al., "Use of dynamic contrast-enhanced MRI to measure subtle blood-brain barrier abnormalities," Magnetic Resonance Imaging, vol. 29, pp. 305-314 (2011).

Van Der Lijn, F. et al., "Automated measurement of local white matter lesion volume," NeuroImage, vol. 59, pp. 3901-3908 (2012).

Cho, H. et al., "Impact of smoking on neurodegeneration and cerebrovascular disease markers in cognitively normal men," European Journal of Neurology, vol. 23, pp. 110-119 (2016).

Wang, B.-R. et al., "Independent Correlation of Serum Homocysteine with Cerebral Microbleeds in Patients with Acute Ischemic Stroke due to Large-Artery Atherosclerosis," Journal of Stroke and Cerebrovascular Diseases, vol. 25, Issue 11, pp. 2746-2751 (Nov. 2016).

Sopacua, C. et al., "The relationship between brain white matter hyperintensities burden and age-related neuropathologies is location dependent," International Society For Magnetic Resonance in Medicine, ISMRM, vol. 2373 (2017).

Jiang, J. et al., "UBO Detector—A cluster-based, fully automated pipeline for extracting white matter hyperintensities," NeuroImage, vol. 174, pp. 539-549 (2018).

Mito, R. et al., "Investigating microstructural heterogeneity of white matter hyperintensities in Alzheimer's disease using single-shell 3-tissue constrained spherical deconvolution," International Society For Magnetic Resonance in Medicine, ISMRM, vol. 26 (2018).

Griffanti, L. et al., "Classification and characterization of periventricular and deep white matter hyperintensities on MRI: A study in older adults," NeuroImage, vol. 170, pp. 174-181 (2018).

Iordanishvili, E. et al., "Quantitative MRI of cerebral white matter hyperintensities: A new approach towards understanding the underlying pathology," NeuroImage, vol. 202 (2019).

Li, H. et al., "Automatic Brain Structures Segmentation Using Deep Residual Dilated U-Net," BrainLes, vol. 11383, pp. 385-393 (2019).

Khan, W. et al., "Three-tissue compositional analysis reveals in-vivo microstructural heterogeneity of white matter hyperintensities following stroke," NeuroImage, vol. 218 (2020).

Ramzan, F. et al., "Volumetric Segmentation of Brain Regions From MRI Scans Using 3D Convolutional Neural Networks," IEEE Access, vol. 8, pp. 103697-103709 (2020).

Hindenes, L.B. et al., "An incomplete Circle of Willis is not a risk factor for white matter hyperintensities: The Tromsø Study," Journal of the Neurological Sciences, vol. 420 (2021).

Extended European Search Report dated Aug. 1, 2024 as received in Application No. 20926370.6.

* cited by examiner

10000

FIG. 6
(a)
(b)
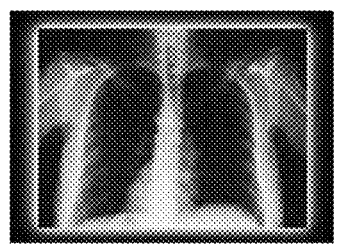
(c)
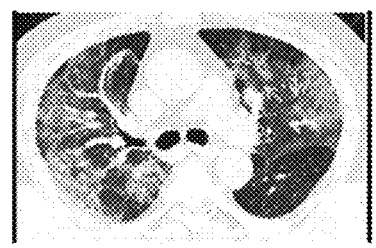
(d)

(a)          (b)

——— PARTIALLY MODIFIED REFERENCE BOUNDARY
– – – ENTIRELY MODIFIED REFERENCE BOUNDARY 1
–  ·  – ENTIRELY MODIFIED REFERENCE BOUNDARY 2

FIG. 36
T1w image
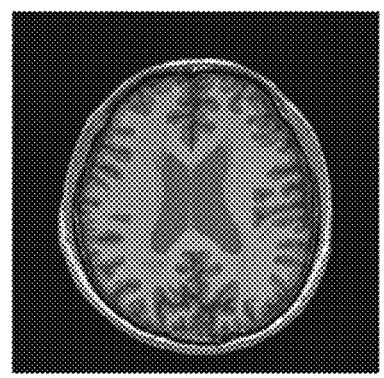
Brain tissue label
FLAIR image
WMH label

PRIMARILY OUTPUT IMAGE    MORPHOLOGICALLY MODIFIED IMAGE

INPUT IMAGE    RESULTANT IMAGE

METHOD OF PROVIDING DIAGNOSIS ASSISTANCE INFORMATION AND METHOD OF PERFORMING THE SAME

TECHNICAL FIELD

The present invention relates to a method of providing diagnosis assistance information by analyzing a medical image and a system for performing the same, and more specifically, a method of segmenting a medical image into a plurality of regions and providing diagnosis assistance information on the basis of a correlation between the plurality of regions, and a system for performing the same.

BACKGROUND ART

In the modern medical treatment field, the demand for various techniques for accurately analyzing a medical image and providing more accurate information about a disease is increasing. In this trend, much attention has been paid to a next-generation medical technology for analyzing a medical image and providing a uniform disease index.

Methods of analyzing a medical image to calculate an index for providing information about a disease have been disclosed in various works of literature. However, in most of the papers about the methods, a doctor's clinical judgment may be involved in analyzing a medical image, and thus information about a disease provided to a patient may be highly likely to be subjective and there may be a large deviation in the information depending on the doctor.

Furthermore, even when image segmentation is performed to provide information about a disease from a medical image, regions to be segmented from the medical image may vary according to a medical image acquisition condition. Therefore, it is difficult to obtain sufficient information about a disease from a certain medical image and thus it is cumbersome to individually segment medical images obtained under various conditions to provide accurate diagnosis assistance information.

DISCLOSURE

Technical Problem

The present invention is directed to providing a uniform criterion in analyzing a medical image to calculate a disease index, thereby eliminating an effect of a doctor's subjective judgment.

The present invention is directed to analyzing a medical image using a highly trained artificial neural network to calculate an objective and uniform disease index.

The present invention is directed to calculating a disease index corresponding to an orientation of a medical image to provide disease information from which effects of a diversity of medical images are removed.

The present invention is directed to obtaining a segmentation result including at least two unique features from a medical image to increase a diversity in providing information about a disease.

Technical Solution

According to an embodiment of the present invention, an image analysis device which provides a diagnostic auxiliary information can be provided, the image analysis device comprises: a communication module obtaining a MRI image related to a brain; a memory storing a program for analyzing the image; and a controller analyzing the MRI image related to the brain using the program stored the memory; wherein the controller distinguishes a ventricle region and a white matter hyperintensity region from the image, sets a reference boundary spaced apart from the ventricle region by a predetermined distance, calculates a first disease index based on the white matter hyperintensity region located within the reference boundary and a second disease index based on the white matter hyperintensity region located outside the reference boundary, and provides a diagnostic auxiliary information based on the first disease index and the second disease index.

According to another aspect of the present invention, a method for providing a diagnostic auxiliary information related to a brain can be provided, the method comprises: obtaining a brain image including a plurality of cells; labeling a feature value reflecting a region of brain to the plurality of cells, wherein the region of brain includes a ventricle and a white matter hyperintensity; determining a reference boundary in the brain image, wherein the reference boundary is defined as a set of cells spaced apart from the ventricle by a predetermined distance; calculating a first disease index related to cells which is located within the reference boundary and is labeled with a feature value indicating the white matter hyperintensity and a second disease index related to cells which is located outside the reference boundary and is labeled with a feature value indicating the white matter hyperintensity; and providing a diagnostic auxiliary information based on the first disease index and the second disease index.

Advantageous Effects

According to the present invention, a uniform criterion can be provided in calculating a disease index from a medical image to provide objective and clear disease information from a patient's condition.

According to the present invention, a method of calculating a criterion reflecting features included in a medical image can be provided to provide a method of providing disease information applicable to a variety of medical images.

According to the present invention, a medical image can be analyzed by a highly trained artificial neural network to provide objective and clear disease information from which a doctor's clinical judgment is removed.

According to the present invention, an artificial neural network trained with at least two medical images having different features can be used to provide accurate disease information from a medical image corresponding to a feature of a patient's disease.

DESCRIPTION OF DRAWINGS

FIG. 6 illustrates examples of a medical image according to an embodiment.

FIG. 36 illustrates an example of a segmentation result using an artificial neural network according to an embodiment.

BEST MODE

Figure 1:
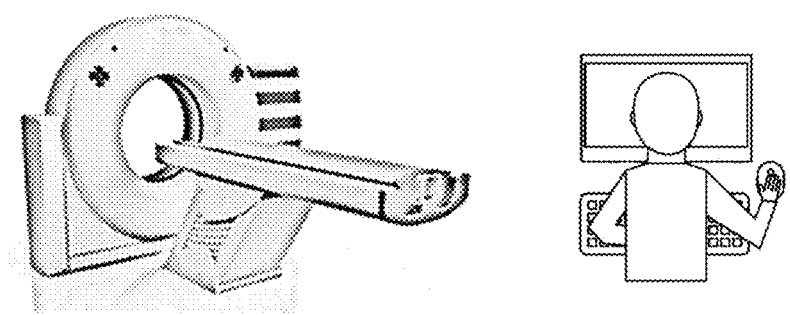
FIG. 1 illustrates an example of a diagnosis assistance information providing system according to an embodiment.

According to an embodiment of the present invention, an image analysis device which provides a diagnostic auxiliary information can be provided, the image analysis device comprises: a communication module obtaining a MRI image related to a brain; a memory storing a program for analyzing the image; and a controller analyzing the MRI image related to the brain using the program stored the memory; wherein the controller distinguishes a ventricle region and a white matter hyperintensity region from the image, sets a reference boundary spaced apart from the ventricle region by a predetermined distance, calculates a first disease index based on the white matter hyperintensity region located within the reference boundary and a second disease index based on the white matter hyperintensity region located outside the reference boundary, and provides a diagnostic auxiliary information based on the first disease index and the second disease index.

According to another aspect of the present invention, a method for providing a diagnostic auxiliary information related to a brain can be provided, the method comprises: obtaining a brain image including a plurality of cells; labeling a feature value reflecting a region of brain to the plurality of cells, wherein the region of brain includes a ventricle and a white matter hyperintensity; determining a reference boundary in the brain image, wherein the reference boundary is defined as a set of cells spaced apart from the ventricle by a predetermined distance; calculating a first disease index related to cells which is located within the reference boundary and is labeled with a feature value indicating the white matter hyperintensity and a second disease index related to cells which is located outside the reference boundary and is labeled with a feature value indicating the white matter hyperintensity; and providing a diagnostic auxiliary information based on the first disease index and the second disease index.

Modes of the Invention

The above-described aspects, features and advantages of the present invention will be more apparent from the following detailed description with reference to the accompanying drawings. However, various changes may be made in the present invention and various embodiments may be implemented and thus example embodiments are illustrated in the drawings and described herein.

In the drawings, thicknesses of each layer or region may be exaggerated for clarity, and when an element or layer is referred to as being "on" or "above" another element or layer, the element or layer may be understood as being directly "on" another element or layer or another element or layer may be interposed between the element or layer and the other element or layer. Throughout the specification, generally, the same reference numerals represent the same elements. In the drawings of embodiments, elements that have the same function and are within the scope of the same idea will be described herein using the same reference numeral.

In the following description, well-known functions or constructions related to the present invention are not described in detail when it is determined that they would obscure the present invention due to unnecessary detail. Numerals (e.g., first, second, etc.) used to describe the present specification are merely identification symbols for distinguishing one element from other elements.

Terms "module" and "unit" used to describe elements of the following description are only intended or interchangeably used to facilitate the making of the specification and should not be understood as having different meanings or functions.

The present disclosure is related to a method of analyzing a medical image and providing diagnosis assistance information related to the medical image and a system for performing the method.

Here, the term "medical image" when used herein should be interpreted to include various images that may be obtained in the medical industry. That is, as used herein, a medical image may be referred to together as images that may be obtained from various devices used in the medical industry. For example, a medical image may be an image obtained by a computed tomography (CT) device such as a magnetic resonance imaging (MRI) device. As another example, a medical image may be a medical image obtained by an X-ray device. A medical image is not limited thereto and may be understood to include all images, e.g., a photograph obtained by a general camera device, which may be obtained in the field of medical industry.

In addition, a target object of a medical image according to an embodiment may include all objects which may be targets in the medical industry. For example, a medical image may be an image of a patient. Specifically, the medical image may be an image of a certain part of the patient's body. As a concrete example, the medical image may be a photograph related to the brain of a patient suspected of having dementia or an image related to the lung of a patient suspected of having lung cancer. In addition, a target object of a medical image according to an embodiment may be tissue collected from a human body.

That is, in the present specification, a medical image may include images of all objects in the medical industry that are captured to obtain disease information included in the images by an image analysis method according to the present invention, and images in forms obtained from various devices available in the medical industry. Although for convenience of description the following description will focus on magnetic resonance imaging (hereinafter referred to as "MRI") related to the brain of the human body, the technical idea of the present disclosure is not limited thereto.

As used herein, "diagnosis assistance information" may refer to comprehensive information that may be objectively judged in relation to a disease on the basis of a medical image. For example, as used herein, diagnosis assistance information may represent the presence or absence of a certain disease. As another example, the diagnosis assistance information may represent a degree of progress of a certain disease. As another example, the diagnosis assistance information may represent severity of a disease. As another example, the diagnosis assistance information may be a numerical value representing the progress of a disease of a certain patient as compared to an average group. In addition, as described above, all information related to a disease that may be judged from a medical image may be referred to together as "diagnosis assistance information".

First, a configuration of a diagnosis assistance information providing system according to an embodiment and examples thereof will be described with reference to FIGS. 1 and 2 below.

Figure 2:
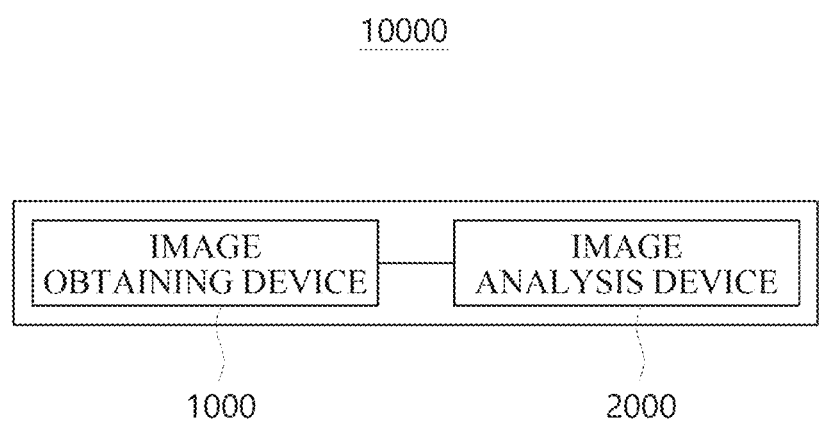
FIG. 2 is a schematic block diagram illustrating a configuration of a diagnosis assistance information providing system according to an embodiment.

FIG. 1 illustrates an example of a diagnosis assistance information providing system according to an embodiment, and FIG. 2 is a schematic block diagram illustrating a configuration of a diagnosis assistance information providing system according to an embodiment.

Referring to FIGS. 1 and 2, a system 10000 according to an embodiment may analyze a medical image to provide diagnosis assistance information.

The system 10000 according to an embodiment may include an image obtaining device 1000 and an image analysis device 2000.

The image obtaining device 1000 may obtain a medical image of an object. Here, the image obtaining device 1000 may refer to various types of devices or systems capable of obtaining a medical image. For example, as shown in FIG. 1, the image obtaining device 1000 may be a magnetic resonance imaging (MRI) device. However, as described above, the image obtaining device 1000 should be understood as not being limited to the MRI device.

The image analysis device 2000 may analyze the medical image obtained by the image obtaining device 1000 and provide diagnosis assistance information. Specifically, the image analysis device 2000 may extract various indexes related to a disease from the medical image and calculate diagnosis assistance information on the basis of the extracted indexes. The analyzing of the medical image by the image analysis device 2000 may be described in detail below.

In addition, the image obtaining device 1000 and the image analysis device 2000 are described above as separate devices, but they are only examples, and the present invention may include a variety of forms that may be embodied as the diagnosis assistance information providing system 10000. That is, the image analysis device 2000 according to an embodiment may be embodied as a separate server or a program integrated into the image obtaining device 1000. However, for convenience of description, the system 10000 in which the image analysis device 2000 is implemented separately will be described herein.

Configurations of an image obtaining device and an image analysis device according to an embodiment will be described with reference to the accompanying drawings below.

Figure 3:
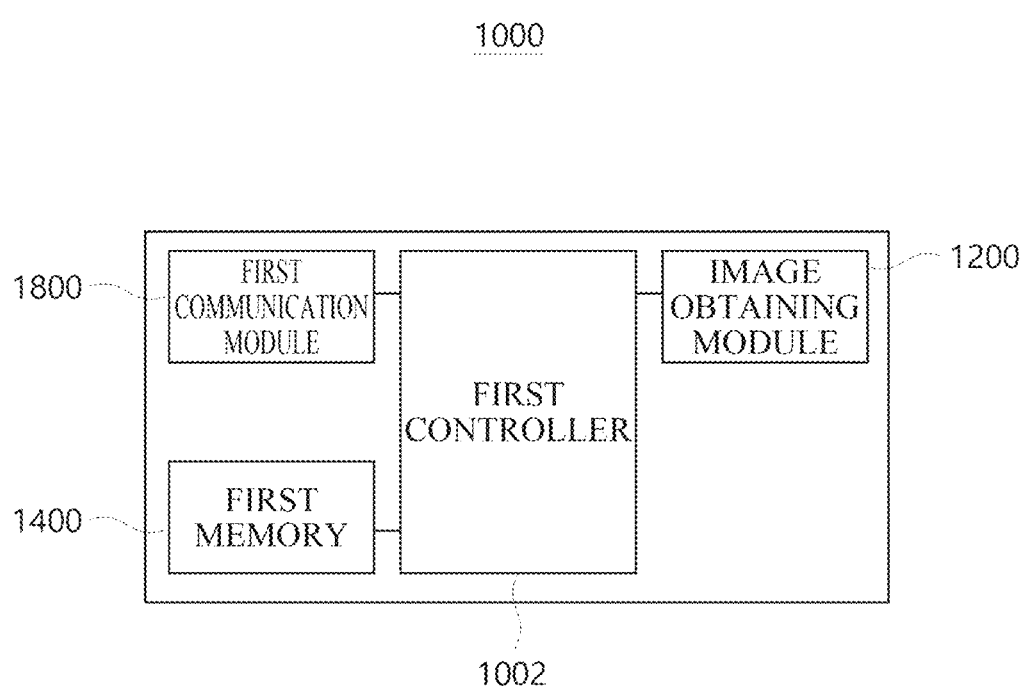
FIG. 3 is a block diagram illustrating a configuration of an image obtaining device according to an embodiment.

FIG. 3 is a block diagram illustrating a configuration of an image obtaining device according to an embodiment.

Referring to FIG. 3, an image obtaining device 1000 according to an embodiment may include a first controller 1002, an image obtaining module 1200, a first memory 1400, and a first communication module 1800.

According to an embodiment, the first controller 1002 may transmit a medical image obtained by the image obtaining module 1200 to the image analysis device 2000 through the first communication module 1800.

Components of the image obtaining device 1000 according to an embodiment will be described below.

According to an embodiment, the image obtaining module 1200 may obtain a result of photographing an object. Here, the image obtaining module 1200 may include components for obtaining various types of medical images. For example, the image obtaining module 1200 may be a component for obtaining an MRI image. As another example, the image obtaining module 1200 may be a component for obtaining an X-ray image or a CT image.

Here, the first controller 1002 may adjust configuration parameters of the image obtaining module. For example, when the image obtaining module 1200 is a component for obtaining an MRI image, the first controller 1002 may adjust a repetition time TR and an echo time TE of an MRI device. Therefore, the MRI device may obtain a T1-weighted image or a T2-weighted image. In addition, the first controller 1002 may adjust a parameter related to an inversion pulse so that the MRI device may obtain a FLAIR image.

The first communication module 1800 according to an embodiment may communicate with an external device or an external server. The image obtaining device 1000 may perform data communication with the image analysis device 2000 or an external device (or a server) through the first communication module 1800. For example, the image obtaining device 1000 may transmit a medical image or data related to the medical image to the image analysis device 2000 or an external device through the first communication module 1800.

The first communication module 1800 is largely divided into a wired type and a wireless type. Because the wired type and the wireless type have merits and demerits, both a wired type communication module and a wireless type communication module may be provided for the image obtaining device 1000.

Here, a representative example of the wired type communication module includes a local area network (LAN) or universal serial bus (USB) communication or other methods may be used.

Here, the wireless type communication module may generally include a communication method based on a wireless personal area network (WPAN) such as Bluetooth or Zig-Bee. However, wireless communication protocol is not limited thereto, and the wireless type communication module may also use a communication method based on wireless local area network (WLAN) such as Wi-Fi or other known communication methods.

The first memory 1400 may store various pieces of information. The first memory 1400 may store various types of data temporarily or semi-permanently. Examples of the first memory 1400 may include a hard disk drive (HDD), a solid-state drive (SSD), a flash memory, a read-only memory (ROM), a random access memory (RAM), etc.

The first memory 1400 may store various types of data necessary to operate the image obtaining device 1000, including an operating system (OS) for driving the image obtaining device 1000 or a program for operating the components of the image obtaining device 1000.

The first controller 1002 according to an embodiment may control overall operations of the image obtaining device 1000. For example, the first controller 1002 may generate a control signal to receive a medical image from the image obtaining module 1200 and transmit the medical image to the image analysis device 2000 via the first communication module 1800.

The first controller 1002 may be embodied as a central processing unit (CPU) or a device similar thereto using hardware, software, or a combination thereof. The first controller 1002 may be provided in a hardware manner as an electronic circuit for processing an electrical signal to perform a control function or may be provided in a software manner as a program or code for driving a hardware circuit.

The image obtaining device 1000 may include a separate power supply or be supplied with power from the outside in a wired or wireless manner and may include a switch for controlling the power supply.

Figure 4:
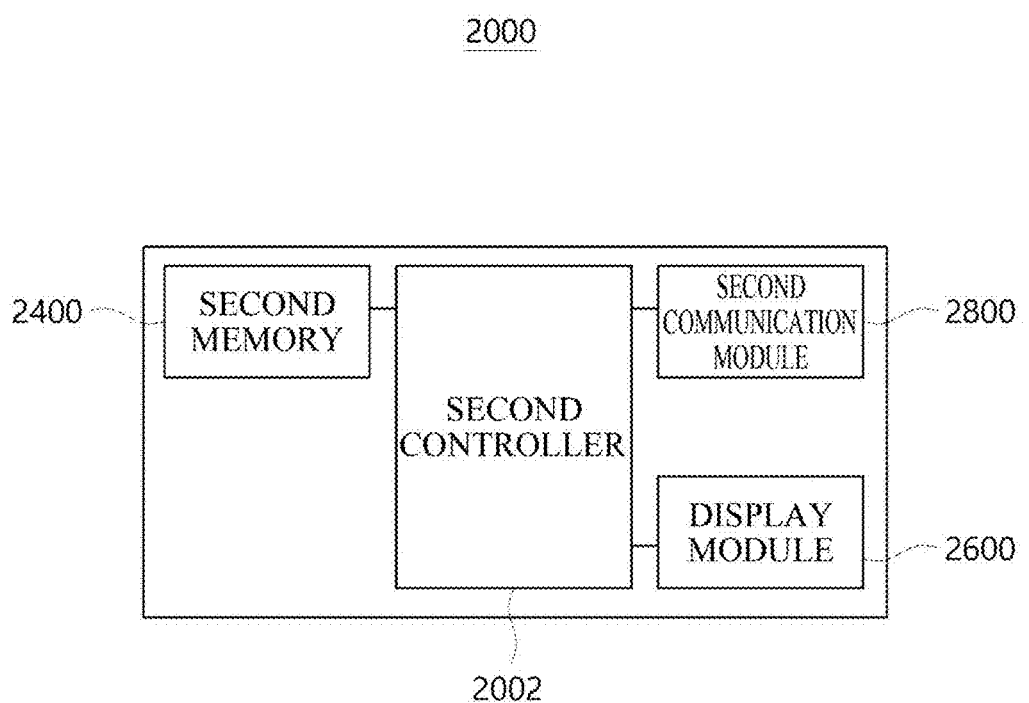
FIG. 4 is a block diagram illustrating a configuration of an image analysis device according to an embodiment.

FIG. 4 is a block diagram illustrating a configuration of an image analysis device according to an embodiment.

Referring to FIG. 4, an image analysis device 2000 may include a second controller 2002, a second memory 2400, a display module 2600, and a second communication module 2800.

According to an embodiment, the second controller 2002 may obtain a medical image from the image obtaining device 1000 through the second communication module 2800 and analyze the medical image using an analysis program stored in the second memory 2400 to calculate diagnosis assistance information from the medical image.

Components of the image analysis device 2000 according to an embodiment will be described below.

The second memory 2400 may store various pieces of information of the image analysis device 2000.

The second memory 2400 may store various types of data necessary to operate the image analysis device 2000, including an operating system for driving the image analysis device 2000 or a program for operating the components of the image analysis device 2000. For example, the second memory 2400 may store a program for processing a medical image and/or a program for analyzing the processed medical image. The programs may be embodied as a machine learning algorithm and will be described in detail below.

Examples of the second memory 2400 may include a hard disk drive (HDD), a solid-state drive (SSD), a flash memory, a read-only memory (ROM), a random-access memory (RAM), etc.

The second memory 2400 may store various types of data necessary to operate the image analysis device 2000, including an operating system (OS) for driving the image analysis device 2000 or a program for operating the components of the image analysis device 2000.

The second communication module 2800 may communicate with an external device or an external server. The image analysis device 2000 may perform data communication with the image obtaining device 1000 or an external device through the second communication module 2800. For example, the image analysis device 2000 may obtain a medical image, which is necessary to provide diagnosis assistance information, from the image obtaining device 1000 using the second communication module 2800.

The second communication module 2800 is largely divided into a wired type and a wireless type. Because the wired type and the wireless type have merits and demerits, both a wired type communication module and a wireless type communication module may be provided for the image analysis device 2000.

Here, a representative example of the wired type communication module includes a local area network (LAN) or universal serial bus (USB) communication, or other methods may be used.

Here, the wireless type communication module may generally include a communication method based on a wireless personal area network (WPAN) such as Bluetooth or Zig-Bee. However, wireless communication protocol is not limited thereto, and the wireless type communication module may also use a communication method based on wireless local area network (WLAN) such as Wi-Fi or other known communication methods.

The second controller 2002 may control overall operations of the image analysis device 2000. For example, the second controller 2002 may generate a control signal to load a program for processing and analyzing image data from the second memory 2400 so as to process and analyze a medical image obtained from the image obtaining device 1000 and to provide a result of processing and analyzing the medical image to an external device or an external server through the second communication module 2800. A method of providing diagnosis assistance information by the image analysis device 2000 will be described in detail below.

The second controller 2002 may be embodied as a central processing unit (CPU) or a device similar thereto using hardware, software, or a combination thereof. The second controller 2002 may be provided in a hardware manner as an electronic circuit for processing an electrical signal to perform a control function or may be provided in a software manner as a program or code for driving a hardware circuit.

In addition, the image analysis device 2000 may further include the display module 2600 for outputting a result of analyzing a medical image. The display module 2600 may be embodied in various forms to provide information to a user. Here, the second controller 2002 may generate a control signal to process and analyze a medical image obtained from the image obtaining device 1000 and to provide a result of processing and analyzing the medical image through the display module 2600.

A method of analyzing a medical image to provide diagnosis assistance information, the method being performed by a diagnosis assistance information providing system according to an embodiment will be described in detail below.

Figure 5:
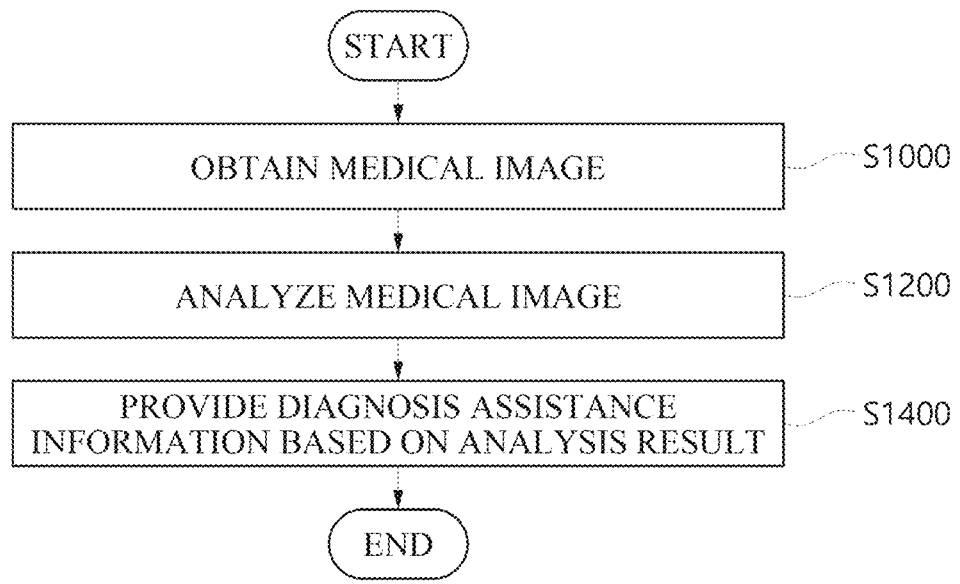
FIG. 5 is an overview flowchart of a method of providing diagnosis assistance information by a diagnosis assistance information providing system according to an embodiment.

FIG. 5 is an overview flowchart of a method of providing diagnosis assistance information by a diagnosis assistance information providing system according to an embodiment.

Referring to FIG. 5, the method of providing diagnosis assistance information according to an embodiment may include obtaining a medical image (S1000), analyzing the obtained medical image (S1200), and providing diagnosis assistance information on the basis of a result of the analyzing (S1400).

First, the diagnosis assistance information providing system 10000 according to an embodiment may obtain a medical image from an object. Specifically, the image obtaining device 1000 may obtain a medical image from an object, such as a patient or a sample, to obtain diagnosis assistance information. More specifically, the image obtaining module 1200 included in the image obtaining device 1000 may obtain a medical image by imaging an object and transmit the obtained medical image to the image analysis device 2000 through the first communication module 1800. Here, a plurality of medical images may be obtained. That is, the image obtaining device 1000 may obtain a plurality of tomographic images of an object captured in a specific direction or with respect to a specific plane from an object.

Here, the plurality of medical images may include three-dimensional (3D) information. That is medical images may be obtained as 3D images.

Here, the specific direction and the specific plane may include information about all directions and planes, such as a transverse plane, a sagittal plane, and a coronal plane, which may be obtained from to the object.

Thereafter, the diagnosis assistance information providing system 10000 may analyze the medical image (S1200). The image analysis device 2000 may analyze the medical image transmitted from the image obtaining device 1000. Specifically, the second controller 2002 may analyze the medical image received through the second communication module 2800 using a program, for image analysis, stored in the second memory 2400. For example, the second controller 2002 may segment the medical image using the program stored in the second memory 2400.

Thereafter, the diagnosis assistance information providing system 10000 may obtain diagnosis assistance information on the basis of a result of analyzing the medical image (S1400). That is, the image analysis device 2000 may obtain diagnosis assistance information included in the medical image from the result of analyzing the medical image using a program for obtaining diagnosis assistance information that is stored in the second memory 2400. The second controller 2002 may transmit diagnosis assistance information calculated through the second communication module 2800 to an external device or an external server or may output diagnosis assistance information using the display module 2600 that is provided separately.

A summary of the method of providing diagnosis assistance information, which is performed by the diagnosis assistance information providing system 10000, according to an embodiment has been described above. The operations of the method of providing diagnosis assistance information, which is performed by the diagnosis assistance information providing system 10000, and sub-operations thereof will be described below.

First, in relation to the obtaining of the medical image (S1000), examples of various medical images that may be obtained by the image obtaining device 1000 according to an embodiment will be described.

FIG. 6 illustrates examples of a medical image according to an embodiment.

Referring to FIG. 6, according to an embodiment, a medical image may be obtained by the image obtaining device 1000 implemented in various forms. The medical image may be an image captured by a variety of CT devices. As described above, the medical image may be a tomographic image set including a plurality of slice images.

For example, the medical image may be an MRI image captured by an MRI device. FIGS. 6A and 6B illustrate various parts of a patient's body photographed by an MRI device. As another example, the medical image may be an X-ray image captured by an X-ray device. FIG. 6C illustrates an X-ray image of a patient captured by an X-ray device. As another example, the medical image may be a CT image captured by a CT device. FIG. 6D illustrates a CT image of a patient captured by a CT device.

Alternatively, the medical image according to an embodiment may be an image of any of various parts of the body. Referring to FIG. 6, the medical image may be an image of part of a patient's body, including an organ such as brain or lung, skeleton such as spine, and neural structure.

Information included in a medical image according to an embodiment may vary according to a configuration parameter of the image obtaining device 1000 for obtaining a medical image.

Figure 7:
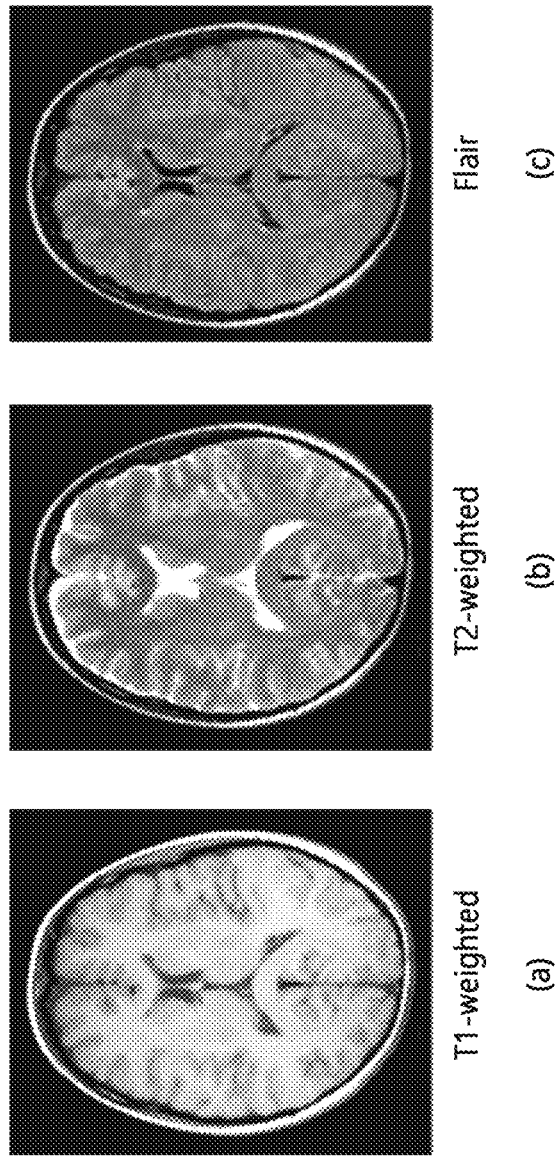
FIG. 7 illustrates examples of a medical image according to various acquisition conditions according to an embodiment.

FIG. 7 illustrates examples of a medical image according to various acquisition conditions according to an embodiment.

Referring to FIG. 7, the image obtaining device 1000 according to an embodiment may obtain various images according to parameters set thereby. For example, when the image obtaining device 1000 is embodied as an MRI device, the image obtaining device 1000 may adjust a parameter related to a magnetic condition to obtain a medical image containing various pieces of information.

More specifically, the image obtaining device 1000 may set a parameter to have a short TR/TE time so as to obtain a T1-weighted image. The T1-weighted image is useful to clearly identify an anatomical structure due to high signal strength. That is, the T1-weighted image is generally used to determine anatomical features of the human body.

In addition, the image obtaining device 1000 may obtain a T2-weighted image by setting a parameter to have a long TR/TE time and obtain a fluid attenuated inversion recovery (FLAIR) image using an inversion pulse. The T2-weighted image and the FLAIR image are characterized in that a moisture-containing region looks white and may be useful in detecting a lesion region due to a high water content of the lesion region.

In addition, a diffusion weighted image (DWI) or a medical image captured using a special imaging technique such as positron emission computed tomography (PET) or functional magnetic resonance imaging (fMRI) may be included in the technical idea of the present invention.

Examples of various medical images that may be obtained in the obtaining of the medical image (S1000) according to an embodiment have been described above. Sub-operations of the analyzing of the obtained medical image (S1200) will be described below.

Figure 8:
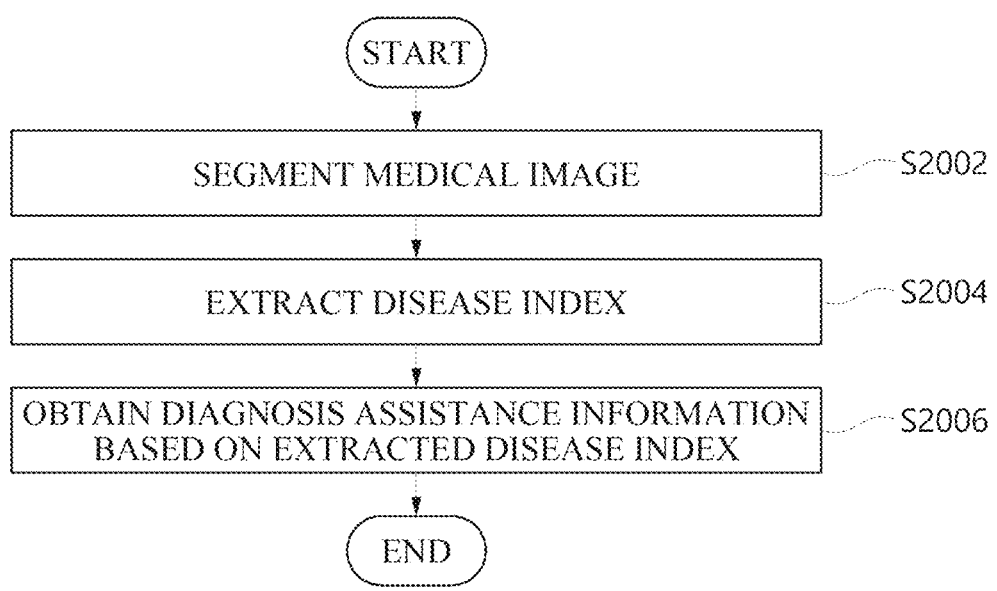
FIG. 8 is a detailed flowchart of analyzing a medical image by an image analysis device according to an embodiment.

FIG. 8 is a detailed flowchart of analyzing a medical image by an image analysis device according to an embodiment.

Referring to FIG. 8, the analyzing of the medical image according to an embodiment may include segmenting the medical image (S2002), extracting a disease index from the segmented medical image (S2004), and obtaining diagnosis assistance information on the basis of the extracted disease index (S2006).

First, the image analysis device 2000 may segment the medical image (S2002). For example, the second controller 2002 may segment the medical image using a program for image segmentation that is stored in the second memory 2400. For example, the second controller 2002 may segment a medical image related to the brain according to regions of the brain. Here, the regions of the brain may refer to lesions found in the medical image or refer to structural regions of the brain found in the medical image. That is, the regions of the brain found in the medical image may include all objects that may be identified in the medical image. That is, the second controller 2002 may segment the medical image related to the brain into at least two regions.

The program for image segmentation that is stored in the second memory 2002 may be implemented as a machine learning algorithm, as will be described in detail below.

After the segmenting of the medical image (S2002), the image analysis device 2000 may extract a disease index from the segmented medical image (S2004). Specifically, the second controller 2002 may extract a disease index using the algorithm stored in the second memory 2400 on the basis of each region included in the segmented medical image.

As used herein, the disease index may be defined as an index expressing the relationship between the regions of the brain in the medical image in relation to a certain disease. It will be apparent that various indexes for extracting information about a disease from the medical image, e.g., a Fazekas scale, an age-related white matter change (ARWMC), a posterior atrophy score of parietal atrophy, a medial temporal lobe atrophy score (MTA), orbito-frontal, anterior cingulate, fronto-insula, anterior temporal scale, etc., may be used as the disease index.

After the extracting of the disease index (S2004), the image analysis device 2000 may provide diagnosis assistance information on the basis of the extracted disease index. Specifically, the second controller 2002 may obtain information about a disease from the medical image using the algorithm stored in the second memory 2400 on the basis of the extracted disease index and output an obtained result.

Hereinafter, examples of a medical image segmented to extract a disease index will be described, and thereafter, various embodiments of extracting a disease index from the segmented medical image will be described with reference to FIG. 9.

Figure 9:
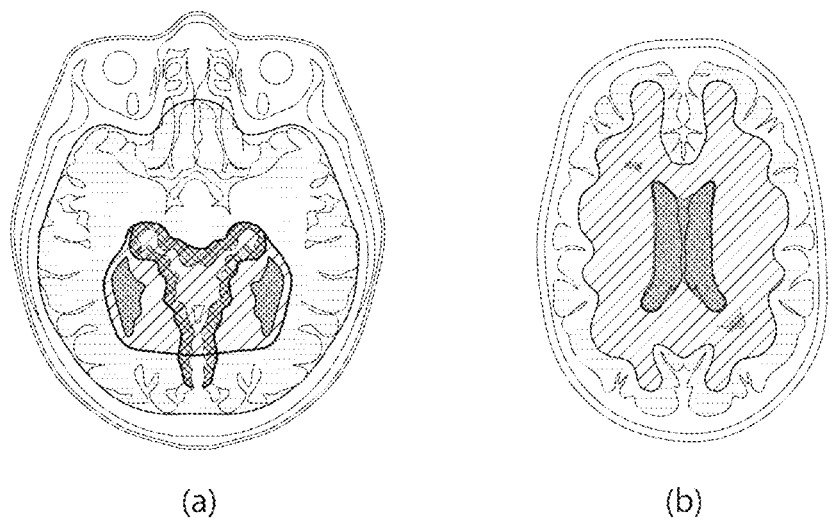
FIG. 9 illustrates examples of a medical image segmented according to an embodiment.

FIG. 9 illustrates examples of a medical image segmented according to an embodiment.

FIG. 9 illustrates examples of a medical image segmented by the image analysis device 2000.

Referring to FIG. 9, the image analysis device 2000 may segment a medical image. Here, the segmentation may be understood to mean that the image analysis device 2000 assigns certain values to unit cells included in the medical image. Specifically, the segmentation may refer to labeling, by the second controller 2002, a pixel or a voxel included in the medical image with a feature value. For example, the second controller 2002 may label a plurality of pixels included in the medical image with a feature value representing a region of the brain.

The image analysis device 2000 may segment the medical image to correspond to a form of the medical image. Here, the form of the medical image may correspond to an acquisition condition under which the medical image is obtained. For example, when a medical image is captured under a particular magnetic condition, the medical image may be in a form of a T1-weighted image. In the following description, the terms "form of a medical image" and "acquisition condition of a medical image" will be interchangeably used for convenience of description but the technical idea of the present invention should not be construed as being limited thereby. Furthermore, a feature (e.g., an anatomical or lesion feature) of a medical image may vary according to the form or acquisition condition of the medical image and thus the term "feature of a medical image" may be interchangeably used herein with the terms "form of a medical image" and "acquisition condition of a medical image".

Specifically, the second controller 2002 may segment a medical image using a program for image segmentation that is stored in the second memory 2400 to reflect features of the medical image.

The second controller 2002 may label a pixel included in the medical image with a value representing a region of the brain. That is, when the medical image is a FLAIR image, the second controller 2002 may label pixels classified into white matter, gray matter, a ventricle, etc. with values corresponding thereto For example, FIG. 9A shows segmentation of a T1-weighted MRI image by the image analysis device 2000, and FIG. 9B shows segmentation of a T2-FLAIR MRI image by the image analysis device 2000.

As shown in the drawing, anatomical features of the brain may be easily grasped from the T1-weighted MRI image of FIG. 9A. That is, when the image analysis device 2000 segments the T1-weighted MRI image, the image analysis device 2000 may segment the T1-weighted MRI image such that parts of the brain may be distinguished from each other. For example, the image analysis device 2000 according to an embodiment may segment a brain image such that organs of the brain, e.g., cerebrum, cerebellum, diencephalon, and hippocampus, parts of the brain, e.g., temporal lobe, frontal lobe, and occipital lobe, or a combination thereof may be distinguished from one another. As such, when diagnosis assistance information is obtained by analyzing the T1-weighted MRI image in which the anatomical feature of the brain is easily observed, the image analysis device 2000 may easily analyze information about a disease, e.g., atrophic Alzheimer, related to the anatomical features of the brain.

A lesion feature of the brain may be easily identified in the T2 Flair MRI image of FIG. 9B. When the image analysis device 2000 according to an embodiment segments the T2-FLAIR MRI image, the image analysis device 2000 may segment the medical image so that a lesion feature of the brain may be identified. Here, the lesion feature of the brain may be detected through white matter hyperintensity (hereinafter referred to as "WMH") observed in the medical image. That is, the image analysis device 2000 may segment the medical image such that the WMH, substances of the brain, or other regions of the brain may be distinguished in the T2-FLAIR MRI image. Here, the substances of the brain (or a human head) may include white matter, gray matter, a skull, and the like and include a ventricle and the like in other regions of the brain. The image analysis device 2000 may extract a disease index on the basis of the relationship between the position of the WMH and the other elements of the brain, as will be described in detail below.

The drawing is described focusing on, for example, the T1-weighted MRI image and the T2-FLAIR MRI image, but the technical idea of the present invention is not limited thereto and MRI images captured under other magnetic conditions such as DWI and SWI or medical images captured by other imaging devices such as an X-ray device and a CT device may be used.

Alternatively, the image analysis device 2000 may segment a medical image having a particular feature (i.e., a medical image obtained under a particular acquisition condition) to include information about other features. Specifically, the second controller 2002 may perform segmentation using the machine learning algorithm stored in the second memory 2400 such that not only a first feature but also a second feature information may be included in a medical image captured under a first condition and having the first feature where the second feature information is obtained when the medical image is captured under a second condition. For example, when a T2-FLAIR MRI image is segmented, the image analysis device 2000 may segment the T2-flair MRI image to include anatomical information that may be observed in a T1-weighted MRI image. This will be described in detail with reference to the drawings below.

An embodiment of a method of extracting a disease index from a segmented medical image will be described in detail with reference to the drawings below.

Figure 10:
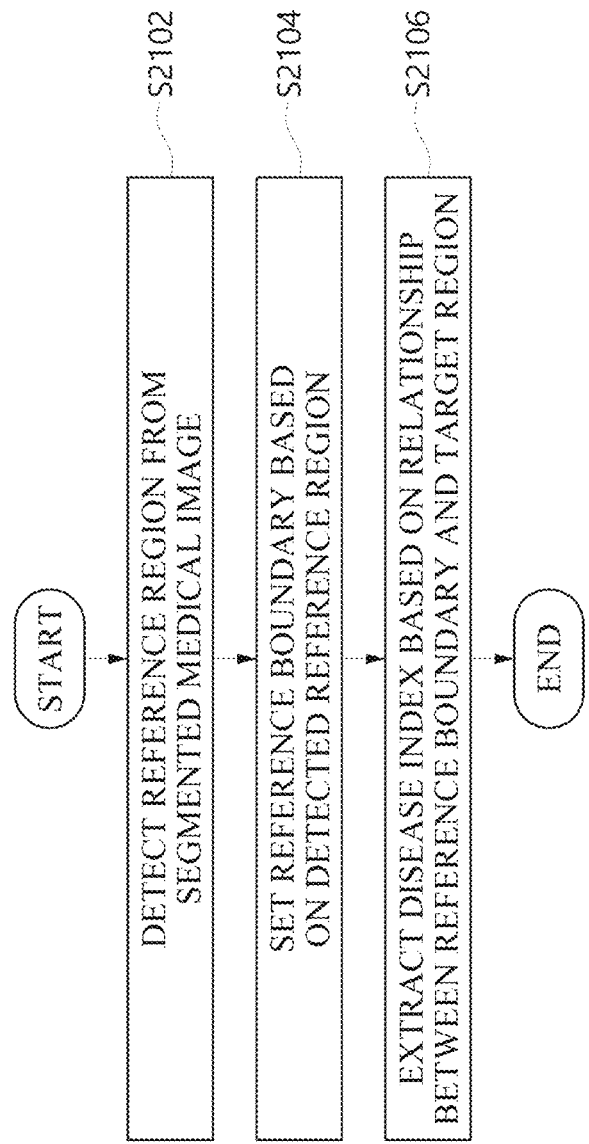
FIG. 10 is a flowchart of an example of a method of extracting a disease index from a medical image according to an embodiment.
Figure 11:
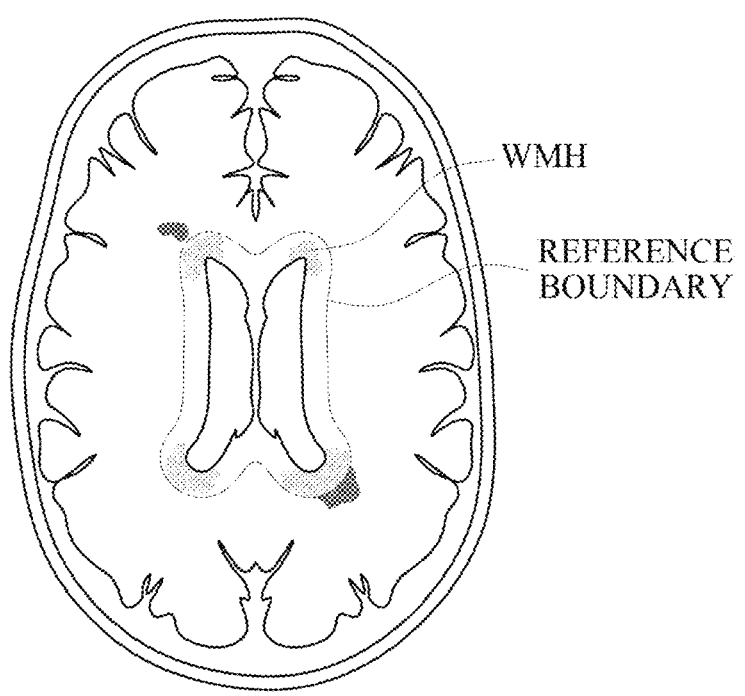
FIG. 11 illustrates an example of a medical image in which a reference region and a reference boundary are shown according to an embodiment.
Figure 12:
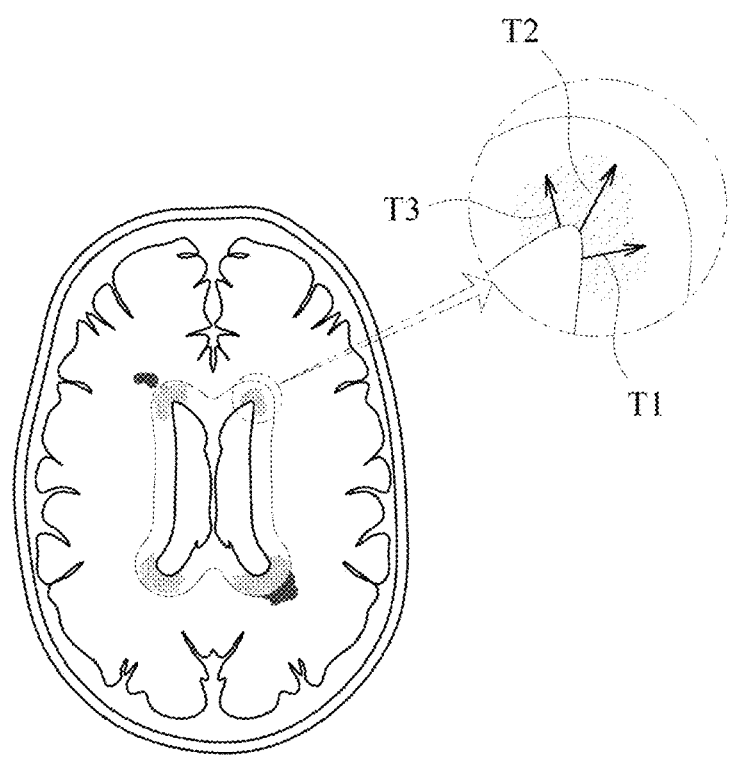
FIG. 12 illustrates an example of a process of obtaining region information of a target region according to an embodiment.
Figure 13:
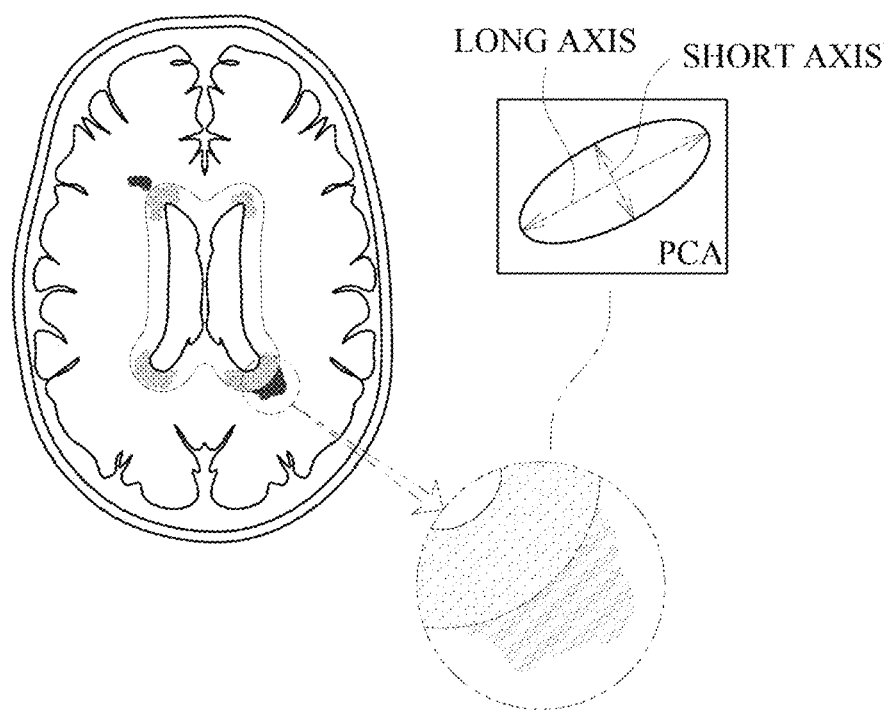
FIG. 13 illustrates another example of a process of obtaining region information of a target region according to an embodiment.
Figure 14:
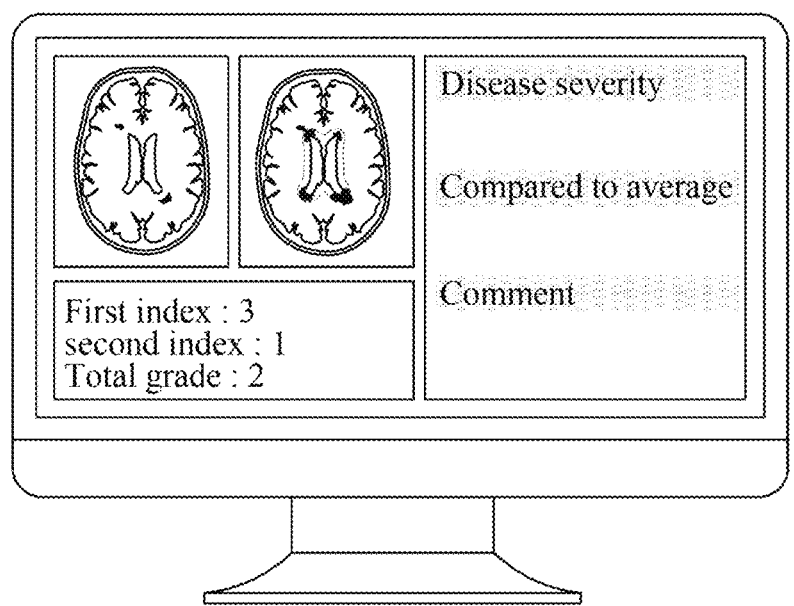
FIG. 14 illustrates an example of providing diagnosis assistance information obtained on the basis of a calculated disease index according to an embodiment.

FIG. 10 is a flowchart of an example of a method of extracting a disease index from a medical image according to an embodiment. FIG. 11 illustrates an example of a medical image in which a reference region and a reference boundary are shown. FIG. 12 illustrates an example of obtaining region information of a target region. FIG. 13 illustrates another example of obtaining region information of a target region. FIG. 14 illustrates an example of providing diagnosis assistance information obtained on the basis of a calculated disease index.

First, a brief flow will be described with reference to FIG. 10. In an embodiment, a method of extracting a disease index from a medical image segmented by the image analysis device 2000 may include detecting a reference region from the segmented medical image (S2102), setting a reference boundary on the basis of the detected reference region (S2104), and extracting a disease index on the basis of the relationship between the reference boundary and a target region (S2106).

The image analysis device 2000 may detect a reference region from a segmented medical image (S2102). Specifically, the second controller 2002 may detect pixels labeled to indicate the reference region in the segmented medical image and determine a set of the pixels as the reference region. Here, the reference region may refer to a region included in the medical image and serving as a criterion for calculation of a certain disease index, as will be described below. For example, the reference region may be a ventricular region. As another example, the reference region may be a white matter region.

Here, the reference region may be a region obtained by adding a buffer region having a certain region or more to a set of pixels labeled to indicate the reference region. The reference region may be defined as a region obtained by removing certain outer pixels from the set of pixels labeled to indicate the reference region.

Alternatively, the image analysis device 2000 may detect a region corresponding to an object to be analyzed from the segmented medical image. Specifically, the second controller 2002 may detect pixels labeled to indicate the object to be analyzed and determine a set of the pixels as a region to be analyzed (hereinafter referred to as a target region). Here, the target region may refer to a region which may be included in the medical image and may be a region to be analyzed for calculation of a certain disease index, as will be described below. For example, the target region may refer to a WMH region. A method of detecting the target region is similar to the above-described method of detecting the ventricular region, and thus a detailed description thereof will be omitted here.

When the reference region is detected, the image analysis device 2000 may set a reference boundary on the basis of the detected reference region (S2104). Specifically, the second controller 2002 may set, as a reference boundary, a boundary spaced a predetermined distance from the ventricular region detected in the medical image.

Here, the reference boundary may refer to a boundary serving as a criterion for deriving the relationship between the reference region and the target region to extract a disease index, as will be described below. That is, when a disease index such as the Fazekas scale is used in judging disease information related to Alzheimer's disease, the positional relationship between the ventricle and the WMH may be used as a significant index, and the reference boundary may be used as a criterion for understanding the positional relationship between the ventricle and the WMH. In this case, the ventricle may be determined as a reference region of the Fazekas scale, and the WMH may be determined as a target region of the Fazekas scale.

Here, a predetermined distance from a point on the reference region may be calculated to obtain the reference boundary. That is, for example, the reference boundary may refer to a set of pixels spaced the predetermined distance from pixels outside the reference region. In this case, a reference direction with respect to the predetermined distance may be a normal direction with respect to a boundary of the reference region. As another example, the reference boundary may refer to a set of pixels spaced the predetermined distance from the center of the reference region.

The reference boundary will be described with reference to FIG. 11 below.

FIG. 11 shows a result of segmenting a T2-FLAIR MRI image into ventricle, WMH, white matter, gray matter, skull, etc.

The image analysis device 2000 may use the Fazekas scale as a disease index. Specifically, the second controller 2002 may determine a ventricular region as a reference region and a WMH region as a target region to calculate a Fazekas scale. Here, the second controller 2002 may be set a set of pixels spaced a predetermined distance from a pixel labeled as a ventricle may be set as a reference boundary as a reference boundary for calculating the Fazekas scale. Alternatively, the reference boundary may be calculated from pixels outside the ventricular region, and the predetermined distance may be calculated to be 10 mm. However, 10 mm is only an example and the predetermined distance may be determined to be in a range of 5 mm to 15 mm.

FIG. 11 illustrates that WMH is present inside and outside the reference boundary. The WMH present inside and outside the reference boundary may be an important factor in determining diagnosis assistance information. Specifically, the relationship between information associated with a region (hereinafter referred to as 'region information') of WMH and the reference boundary is closely related to the diagnosis assistance information. A method of calculating the region information of the WMH from the medical image segmented with respect to the WMH will be described with reference to FIGS. 12 to 13 below.

According to medical studies, in general, among regions of the brain, a white matter region relatively close to the ventricular region is likely to be more easily denatured than a white matter region relatively distant from the ventricle region. Therefore, a WMH region near the ventricle included in the medical image and a WMH region relatively distant from the ventricle may include different information related to a disease. Accordingly, it is necessary to analyze a WMH region included in the medical image in consideration of a distance to the ventricle.

FIGS. 12 and 13 illustrate examples of a method of obtaining region information related to a target region in consideration of a distance between the reference region and the target region.

Referring to FIG. 12, the image analysis device 2000 according to an embodiment may obtain region information of a target region in a medical image. Specifically, the second controller 2002 may obtain the region information of the target region in the medical image on the basis of a segmentation result. Here, the region information may refer to a thickness or area of a certain region. As described later, when the medical image is a 3D image, the region information may refer to volume.

First, when a disease index is calculated on the basis of the Fazekas scale, a method of calculating region information of a target region near a reference region included in the medical image, i.e., a target region within a reference boundary as described above, according to an embodiment will be described below.

The image analysis device 2000 may obtain the region information of the target region on the basis of the distance from the reference region to the target region. Specifically, the second controller 2002 may calculate the region information of the target region on the basis of a distance from a region labeled as the reference region to a region labeled as the target region in the medical image.

For example, the second controller 2002 may calculate a thickness of a WMH region on the basis of a distance from a region labeled as a ventricle to a region labeled as a WMH in the medical image. Here, a criterion of the distance may be defined in a normal direction with respect to a boundary of the region labeled as the ventricle. In addition, a longest length among calculated thicknesses of WMH may be measured as the thickness of the WMH. More specifically, the second controller 2002 may determine, as a first point, a WMH region closest in the normal direction to a boundary of the region labeled as the ventricle, determine, as a second point, a WMH region most distant in the normal direction to the boundary of the region labeled as the ventricle, and determine a distance between the first and second points as a thickness (width) of the WMH region. Here, when the WMH region is connected (attached) to the ventricle region, the first point may be determined as one point on the ventricle.

In other words, the second controller 2002 may generate rays in the normal direction at the boundary of the ventricular region in the medical image and calculate a thickness of a WMH in consideration of points of contact of the rays and pixels labeled as the WMH. Here, the points of contact of the rays and the pixels labeled as the WMH may include a first point of contact at which a distance between the ventricular region and the WMH region is small and a second point of contact at which a distance between the ventricular region and the WMH region is largest. That is, the second controller 2002 may calculate the thickness (width) of the WMH region in consideration of the distance between the first point of contact and the second point of contact. Here, the first point of contact may be located on the ventricular region as described above.

The method using rays may be applied to WMH within the reference boundary but embodiments are not limited thereto and this method may also apply to WMH beyond the reference boundary.

FIG. 13 illustrates a method of calculating region information with respect to WMH beyond a reference boundary.

Referring to FIG. 13, the image analysis device 2000 may obtain region information of a target region using a principal component analysis. Specifically, the second controller 2002 may extract at least two principal components of the target region using the principal component analysis and calculate the region information of the target region on the basis of the extracted principal components.

For example, the second controller 2002 may extract principal components with respect to at least two axes in a region labeled as WMH in a medical image. Here, the principal component may be extracted in various ways, but it may be extracted with respect to a short axis and a long axis from the region labeled as WMH. When the principal components are extracted, the second controller 2002 may calculate the thickness of the region labeled as WMH on the basis of the extracted principal components.

In other words, the second controller 2002 may perform the principal component analysis on the region labeled as WMH to obtain an orientation and size of the region with respect to the long axis and the short axis and calculate the thickness of the region labeled as WMH on the basis of a length of the region with respect to the long axis. Alternatively, the second controller 2002 may calculate a width of the WMH region.

The method of calculating the region information of the target region to be used to obtain a disease index from the medical image has been described above. In addition, the positional relationship between the target region and the reference region may be considered to obtain the region information of the target region as described above.

A method of extracting a disease index on the basis of the calculated region information of the WMH and the reference boundary will be described with reference to FIG. 10 below.

Referring back to FIG. 10, the image analysis device 2000 may calculate a disease index on the basis of the reference boundary set in the medical image and the region information of the target region (S2106).

Specifically, the second controller 2002 may calculate a disease index in consideration of the correlation between the reference boundary and the target region and the region information of the target region.

Here, the correlation may represent, for example, whether or not WMH is present inside or outside the reference boundary.

As a concrete example, generally, the greater a thickness of WMH, the more serious a disease is, but in a method of extracting a disease index according to an embodiment, not only a thickness of WMH, but also whether the WMH is present inside or outside a reference boundary may be considered.

TABLE 1

| grade | first disease index | second disease index | third disease index |
|---|---|---|---|
| 0 | no white matter lesions | no white matter lesions | calculation in consideration of |
| 1 | "cap" or linear lesions near ventricle | lesions of speckled shape on deep white matter | first disease index and second disease index |
| 2 | lesions in the form of soft "halo" around the ventricle | start of joining of lesion area around ventricle | |
| 3 | lesions of soft "halo" form around ventricle | formation of large confluent region with lesion area around ventricle | |

TABLE 2

| grade | first disease index | second disease index | third disease index |
|---|---|---|---|
| 0 | no WMH | no WMH | when first disease index is 0 and second disease index is 0 |
| 1 | when thickness of white matter lesions inside reference boundary is less than 5 mm | when thickness or length of white matter lesions outside reference boundary is less than 10 mm | when first disease index is grade 1 or 2 and second disease index is grade 1 |
| 2 | when thickness of white matter lesions inside reference boundary is greater than or equal to 5 mm and less than 10 mm | when thickness or length of white matter lesions outside reference boundary is greater than or equal to 10 mm and less than 25 mm | when first disease index is grade 1, 2, or 3 and second disease index is grade 2 or when first disease index is grade 3 and second disease index is grade 1 |
| 3 | when thickness of white matter lesions measured inside reference boundary is 10 mm or more | when thickness or length of white matter lesions outside reference boundary is greater than 25 mm | when second disease index is grade 3 and first disease index is grade 1, 2, or 3 |

Table 1 shows an example of a criterion for calculating a disease index according to a doctor's subjective judgment.

Table 1 shows an example of a criterion for calculating the Fazekas Scale used at existing medical industrial sites. The Fazekas scale is a method of calculating a disease index published in various papers and has been used as a reliable method of calculating a disease index at medical industrial sites. However, as shown in Table 1, in the existing medical industry, a disease index is calculated on the basis of an ambiguous criterion and thus objective diagnosis information or diagnosis assistance information cannot be provided to a patient.

Table 2 shows criteria for calculation of a disease index which is performed by an image analysis device according to an embodiment.

Therefore, referring to Table 2, the image analysis device 2000 according to an embodiment may calculate a disease index according to a clear criterion. Specifically, the second controller 2002 may calculate a disease index from a medical image according to a criterion for calculating a disease index which is stored in the second memory 2400.

Here, the criterion for calculating a disease index by the image analysis device 2000 may be determined on the basis of various diagnosis results or diagnosis assistance results obtained in advance at a medical industrial site. That is, according to an embodiment, the image analysis device 2000 may calculate a disease index from a medical image using a criterion quantified based on a result of analyzing a plurality of medical images which are obtained in advance at a medical industrial site and from which a disease index is calculated.

That is, the image analysis device 2000 may analyze the medical image to determine a disease index to be calculated according to a certain criterion and calculate a grade of the disease index corresponding to the determined disease index. Specifically, the second controller 2002 may determine a reference boundary from a reference region, determine a disease index to be calculated in consideration of the relationship between the reference boundary and a target region, and calculate a grade corresponding to the determined disease index.

Here, the criterion for determining the disease index to be calculated nay be the reference boundary described above. For example, the type of a disease index to be calculated by the image analysis device 2000 may vary according to whether the target region is located inside or outside the reference boundary.

Here, there may be a criterion for identifying a grade of the disease index in the calculation of the same disease index. For example, a predetermined criterion may be a criterion related to region information of the target region.

Referring back to Table 2, a disease index according to an embodiment may include first to third disease indexes. The disease index shown in Table 2 may be the Fazekas scale. The first disease index may represent a disease index related to peri-ventricular white matter, the second disease index may represent a disease index related to deep white matter, and the third disease index may represent a total index calculated in consideration of the first and second disease indexes.

Here, the reference boundary may be used to distinguish between the first disease index and the second disease index. That is, as described above, the second controller 2002 may calculate the first disease index from the target region inside the reference boundary using the reference boundary. The second controller 2002 may calculate the second disease index from the target region outside the reference boundary using the reference boundary.

Grades may be distinguished in the same disease index. That is, the second controller 2002 may calculate a grade corresponding to a certain disease index from a medical image according to a predetermined criterion.

Here, the predetermined criterion may be related to the region information of the target region. For example, when there is no cell indicating the target region or the number of such cells is determined to be equal to or less than a predetermined number, the second controller 2002 may determine the grade of the certain disease index to be 0. As another example, when a thickness of the target region is obtained to be greater than or equal to a first value, the second controller 2002 may determine a grade of a certain disease index to be 1. As another example, when the thickness of the target region is obtained to be greater than or equal to a second value, the second controller 2002 may determine a grade of a certain disease index to be 2. As another example, when the thickness of the target region is obtained to be greater than or equal to a third value or the target region is connected to another target region, the second controller 2002 may determine a grade of a certain disease index to be 3.

That is, referring to the examples shown in Table 2, the second controller 2002 may calculate a first disease index on the basis of a target region inside a reference boundary as a result of analyzing a medical image, and calculate a grade related to the first disease index in consideration of region information of the target region inside the reference boundary.

In addition, the image analysis device 2000 may calculate all values related to the first disease index and a second disease index in the same medical image. When all target regions are located inside and outside the reference boundary as a segmentation result of the medical image, the second controller 2002 may calculate both grades of the first disease index and the second disease index.

Furthermore, the image analysis device 2000 may calculate a third disease index in consideration of the first disease index and/or the second disease index.

FIG. 14 illustrates an example of a display for providing a disease index and diagnosis assistance information based on the disease index according to an embodiment.

Referring to FIG. 14, the image analysis device 2000 may provide diagnosis assistance information on the basis of a disease index. Specifically, the second controller 2002 may obtain a disease index as a result of analyzing a medical image and provide diagnosis assistance information on the basis of the obtained disease index.

Specifically, referring to the drawing, the second controller 2002 may provide a disease index related to the target region inside the reference boundary on the basis of the result of analyzing the medical image. In addition, information about the meaning of the disease index may be provided on the basis of the disease index.

Here, as described above, the disease index may be understood to mean the progress of a disease determined from the medical image or a barometer (criterion) related to severity of the disease. For example, when the criterion of the disease index is the Fazekas scale, the disease index may be expressed as a grade of the Fazekas scale.

Alternatively, the diagnosis assistance information may refer to information related to a disease that may be determined on the basis of the disease index. For example, when the disease index is the Fazekas scale and a certain grade is calculated, the diagnosis assistance information may refer to information about the disease derivable from the disease index, e.g., a current progress of the disease, the difference between the grade and a normal category, the difference between the disease and an average grade of each age, etc.

Diagnosis assistance information, e.g., an average value of each age, a disease index of a normal person, etc., to be compared with the diagnosis assistance information that may be obtained from the medical image may be obtained in advance, stored in the second memory 2400, and continuously updated.

As described above, the image analysis device 2000 may set a clear criterion, extract a disease index from a medical image, and provide diagnosis assistance information on the basis of the extracted disease index, thereby obtaining diagnosis assistance information that is more objective and accurate than information about a disease provided dependent on a doctor's subjective judgement in the medical industry.

A method using a predetermined reference boundary has been described above as an embodiment of a method of providing diagnosis assistance information. However, in order to provide more accurate diagnosis assistance information, it may be necessary to modify a reference boundary in consideration of a feature of a medical image rather than using a fixed reference boundary.

A method of providing diagnosis assistance information using a modified reference boundary according to another embodiment will be described with reference to the drawings below.

First, another example of extracting a disease index and obtaining disease information from a medical image according to an embodiment will be briefly described with reference to FIG. 15.

Figure 15:
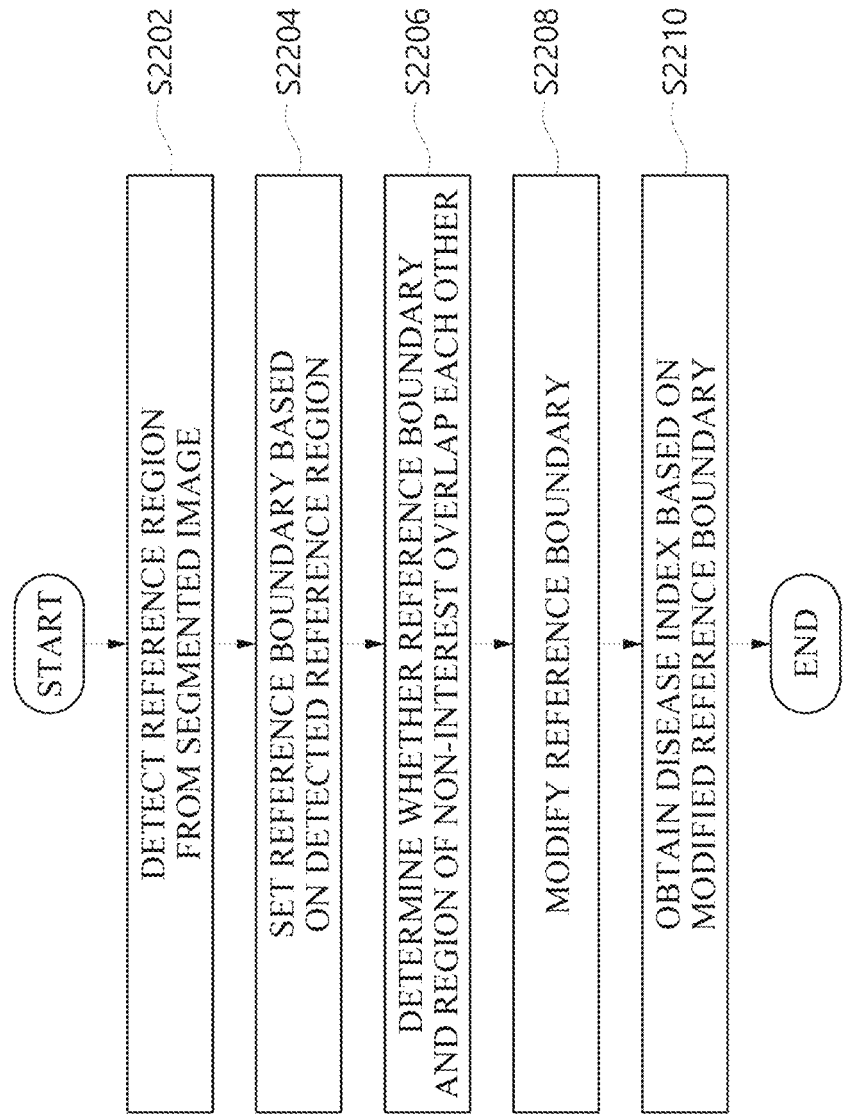
FIG. 15 is a flowchart of an example of a method of providing diagnosis assistance information using a modified reference boundary according to an embodiment.

FIG. 15 is a flowchart of an example of a method of providing diagnosis assistance information using a modified reference boundary according to an embodiment.

Referring to FIG. 15, the method of providing diagnosis assistance information according to an embodiment may include detecting a reference region from a segmented medical image (S2202), setting a reference boundary on the basis of the detected reference region (S2204), determining whether the reference boundary and a region of non-interest overlap each other (S2206), modifying the reference boundary (S2208), and obtaining a disease index on the basis of the modified reference boundary (S2210).

First, the detecting of the reference region (S2202) and the setting of the reference boundary on the basis of the detected reference region (S2204) may be performed by the image analysis device 2000 similarly to the operations performed in the embodiments described above with reference to FIGS. 10 to 14, and thus a detailed description thereof will be omitted here.

When the reference boundary is set, the image analysis device 2000 may determine whether the set reference boundary overlaps a region of non-interest of the segmented medical image (S2206). Specifically, the second controller 2002 may determine whether, in the medical image, a pixel corresponding to the set reference boundary is included in a pixel labeled with a value indicating the region of non-interest. Here, the region of non-interest may be a gray matter region.

Figure 16:
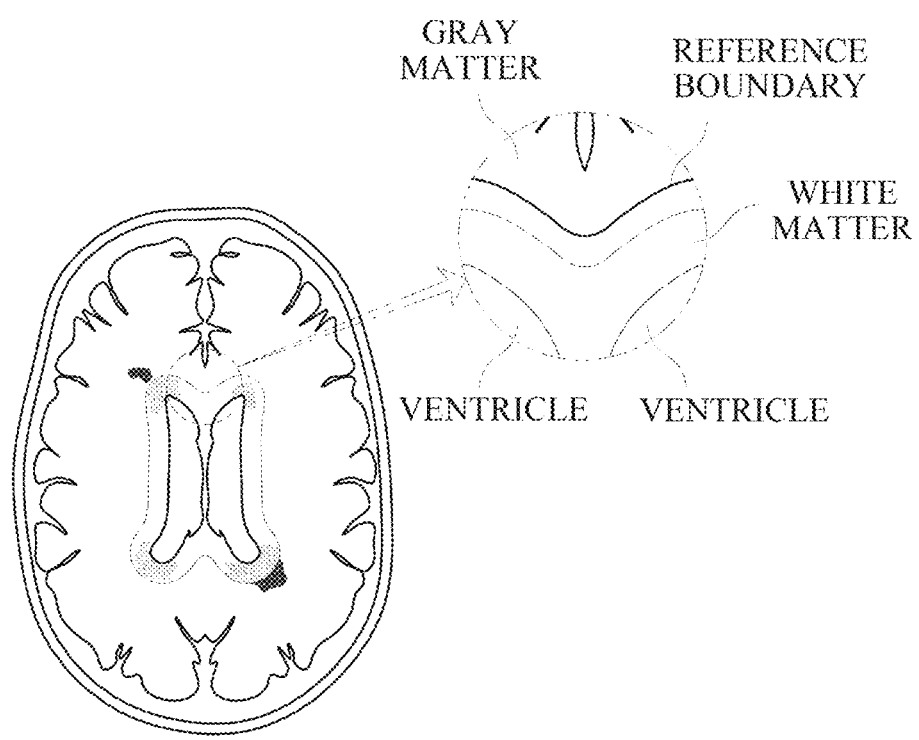
FIG. 16 illustrates a case in which a reference boundary and a region of non-interest overlap each other according to an embodiment.

FIG. 16 will be referred to.

FIG. 16 illustrates a case in which a reference boundary and a region of non-interest overlap each other according to an embodiment.

Referring to FIG. 16, a case in which a reference boundary overlaps a region labeled as gray matter in the medical image is shown.

Generally, WMH occurs in white matter and is not found in gray matter. For this reason, when the reference boundary extends to a gray matter region, a disease index may be inaccurately calculated when the disease index is extracted as in a method of related art and thus diagnosis assistance information based on the disease index is highly probable to be inaccurate information. Therefore, when the reference boundary overlaps the gray matter region or the like, it is necessary to modify the reference boundary and calculate a disease index using the modified reference boundary.

In the following description, a region in which a target region (e.g., WMH) may be observed, such as a white matter region, will be referred to as a "region of interest", and a region in which a target region (e.g., WMH) is not observed, such as a gray matter region, will be referred to as a "region of non-interest".

Thus, after the medical image is segmented and the reference boundary is set, the second controller 2002 may modify the reference boundary when the reference boundary overlaps at least a portion of a region labeled as gray matter (S2208).

Referring back to FIG. 15, when the reference boundary is modified, the image analysis device 2000 may obtain a disease index on the basis of the modified reference boundary (S2210). A method of obtaining the disease index is similar to the embodiments described above with reference to FIGS. 10 to 14, and thus a detailed description thereof will be omitted.

An example of modifying the reference boundary will be described with reference to the drawings below.

Figure 17A:
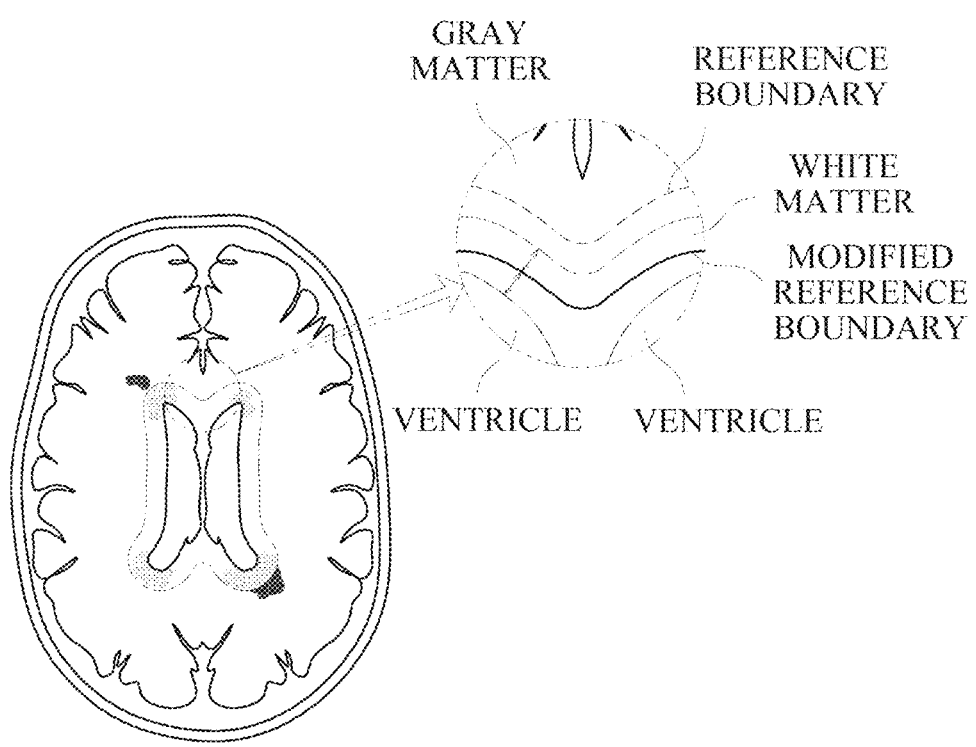
FIGS. 17A and 17B illustrate examples of a method of calculating a modified reference boundary according to an embodiment.
Figure 17B:
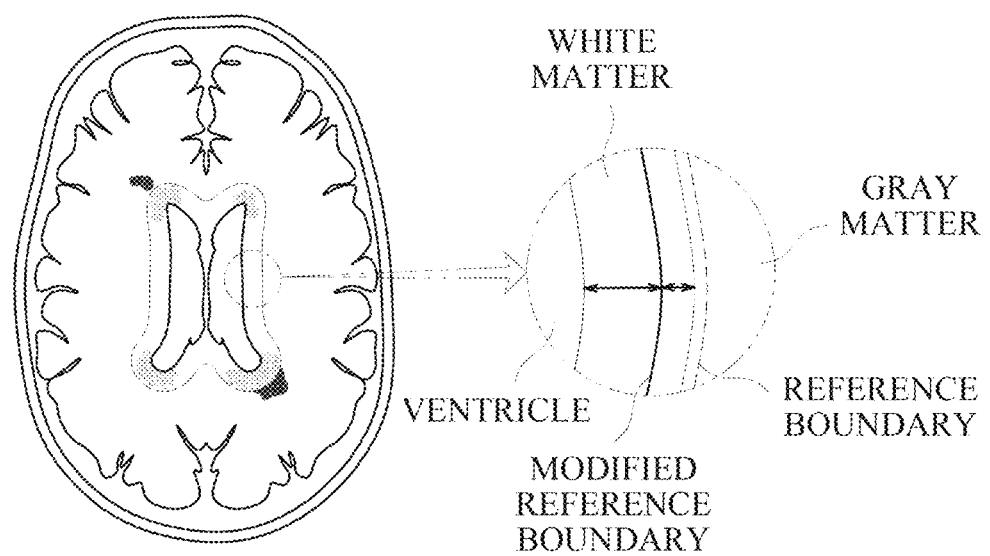

FIGS. 17A and 17B illustrate examples of a method of calculating a modified reference boundary according to an embodiment.

Referring to FIGS. 17A and 17B, the image analysis device 2000 may modify a reference boundary. Specifically, the second controller 2002 may modify the reference boundary such that the modified reference boundary is located between a region labeled as a region of non-interest and a region labeled as a region of interest. Here, the reference boundary may be positioned such that a reference region and the region of non-interest may be internally divided at a predetermined ratio. Here, the predetermined ratio may be set in consideration of various factors. For example, the predetermined ratio may be determined in consideration of the distance between the region of non-interest and the reference region. That is, the second controller 2002 may modify the reference boundary while reflecting various factors that may be considered in the medical image, including the distance between the reference region and the region of non-interest, the position of the reference boundary overlapping the region of non-interest, and/or the shape of the reference region.

Specifically, referring to the drawings, FIG. 17A illustrates that the distance between a region of non-interest (gray matter) and a reference region (ventricle) is relatively small and thus a reference boundary overlaps a relatively large part of the region of non-interest. In this case, the second controller may modify the reference boundary in consideration of the distance between the region of non-interest and the reference region such that the modified reference boundary is positioned at a midpoint between a gray matter region and a ventricular region (such that the distance between a ventricle and gray matter is internally divided at a ratio of 5:5).

FIG. 17B illustrates that the distance between a region of non-interest (gray matter) and a reference region (ventricle) is relatively large and that a reference boundary overlaps a relatively small part of the region of non-interest. In this case, the second controller 2002 may modify the reference boundary such that the modified reference boundary is closer to the region of non-interest.

According to an embodiment, a reference boundary determined in one medical image may overlap a plurality of regions of non-interest. That is, the cases of FIGS. 17A and 17B may occur in one medical image.

In this case, the second controller 2002 may modify the reference boundary such that a first section and a second section that overlap the region of non-interest within the reference boundary have different ratios. For example, the second controller 2002 may modify the reference boundary in the first section as described above with reference to FIG. 17A and modify the reference boundary in the second section as described above with reference to FIG. 17B.

In other words, the second controller 2002 may modify the reference boundary such that a ratio between a distance from the reference region to the reference boundary and a distance from the reference boundary to the region of non-interest is a first value at a position at which the distance between the region of non-interest and the reference region is a first distance and is a second value at a position at which the distance between the region of non-interest and the reference region is a second distance. Here, when the second distance is greater than the first distance, the reference boundary may be modified such that the second value is smaller than the first value. For example, as the distance between the reference region and the region of non-interest increases, the modified reference boundary may be tilted toward the region of non-interest.

As a concrete example, the second controller 2002 may modify the reference boundary such that the distance between gray matter and a ventricle is internally divided at a ratio of 5:5 by the reference boundary in the first section in which the distance between gray matter and a ventricle is relatively small and is internally divided at a ratio of 3:7 by the reference boundary in the second section in which the distance between gray matter and a ventricle is relatively large. Here, a ratio at which the distance between the gray matter and the ventricle is internally divided may be predetermined.

Alternatively, the second controller 2002 may modify the reference boundary only in a region in which the reference boundary and the region of non-interest overlap each other or modify the entire reference boundary. Alternatively, the second controller 2002 may modify the reference boundary in a buffer region in addition to the region in which the reference boundary and the gray matter region overlap each other. This will be described in detail with reference to FIG. 18 below.

Figure 18:
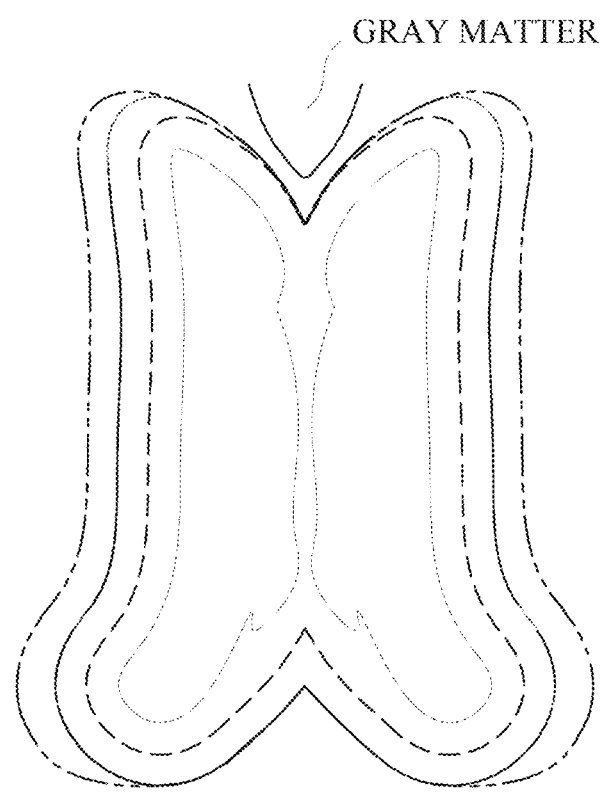
FIG. 18 illustrates an example of a partially modified reference boundary and an entirely modified reference boundary according to an embodiment.

FIG. 18 illustrates an example of a partially modified reference boundary and an entirely modified reference boundary according to an embodiment.

Referring to FIG. 18, the image analysis device 2000 may modify a reference boundary entirely or partially. Specifically, the second controller 2002 may modify the reference boundary entirely or partially in consideration of the relationship between a reference region and a region of non-interest.

For example, when the distance between only a part of the reference region and only a part of the region of non-interest is small, the reference boundary may be modified only in a section of the reference boundary corresponding to the parts, and when the distance between the reference region and the region of non-interest is measured to be substantially the same, the entire reference boundary may be modified. However, this is only an example, and there may be various cases in which the reference boundary may be entirely or partially modified.

Examples of the cases will be described with reference to the drawings below. An entirely modified reference boundary and a partially modified reference boundary are shown in the drawings.

First, an example in which the entire reference boundary is modified will be described below.

The image analysis device 2000 may modify the entire reference boundary. Specifically, the second controller 2002 may modify the entire reference boundary in consideration of the distance between a reference region and a region of non-interest.

The second controller 2002 may modify the entire reference boundary to correspond to the modifying of the reference boundary in the section in which the reference boundary and the region of non-interest overlap each other.

Alternatively, the second controller 2002 may modify the reference boundary in consideration of the distance between the reference boundary and the region of non-interest in all sections of the reference boundary, as well as the section in which the reference boundary and the region of non-interest overlap each other.

For example, the second controller 2002 may modify the entire reference boundary to correspond to a position at which the distance between a region of non-interest of a first region and the reference region is internally divided, in consideration of the distance between a region of non-interest in a first region and the reference region.

Alternatively, the second controller 2002 may modify the entire reference boundary in consideration of the distance between overall regions of the reference region and the region of non-interest with respect to all sections of the reference boundary.

Alternatively, the image analysis device 2000 may modify only a part of the reference boundary. Specifically, the second controller 2002 may modify only a section of the reference boundary corresponding to a section in which the reference boundary and the region of non-interest overlap each other. Here, the second controller 2002 may modify the reference boundary in the section in which the reference boundary and the region of non-interest overlap each other and to which a buffer section is added or may modify the reference boundary only in the section from which some sections are removed.

In other words, the second controller 2002 may determine the reference boundary such that the distance between the reference boundary and the reference region is a first distance in a section in which the distance between the reference boundary and the region of non-interest is less than a predetermined distance and is a second distance in a section in which the distance between the reference boundary and the region of non-interest is greater than the predetermined distance. Here, the predetermined distance may correspond to the distance between the reference boundary and the reference region described above with reference to FIGS. 10 to 14.

Referring to the drawing, it is shown that all of a partially modified reference boundary, an entirely modified reference boundary 1, and an entirely modified reference boundary 2 have substantially the same shape in a section in which a region of non-interest (gray matter) and a reference region are close to each other. However, the entirely modified reference boundary 1 is spaced the same distance from the reference region even in a section which the distance between the region of non-interest and the reference region is large. In contrast, the entirely modified reference boundary 2 is determined such that in all sections of the reference boundary, the reference boundary is positioned to internally divide the region of non-interest and the reference region at a predetermined ratio.

However, even in the case of the partially modified reference boundary, a modified region of the reference boundary and an original reference boundary should be smoothly connected so that the modified reference boundary may have a smooth shape.

The relationship between the original reference boundary and a modified reference boundary when the reference boundary is partially modified will be described with reference to the drawings below.

Figure 19:
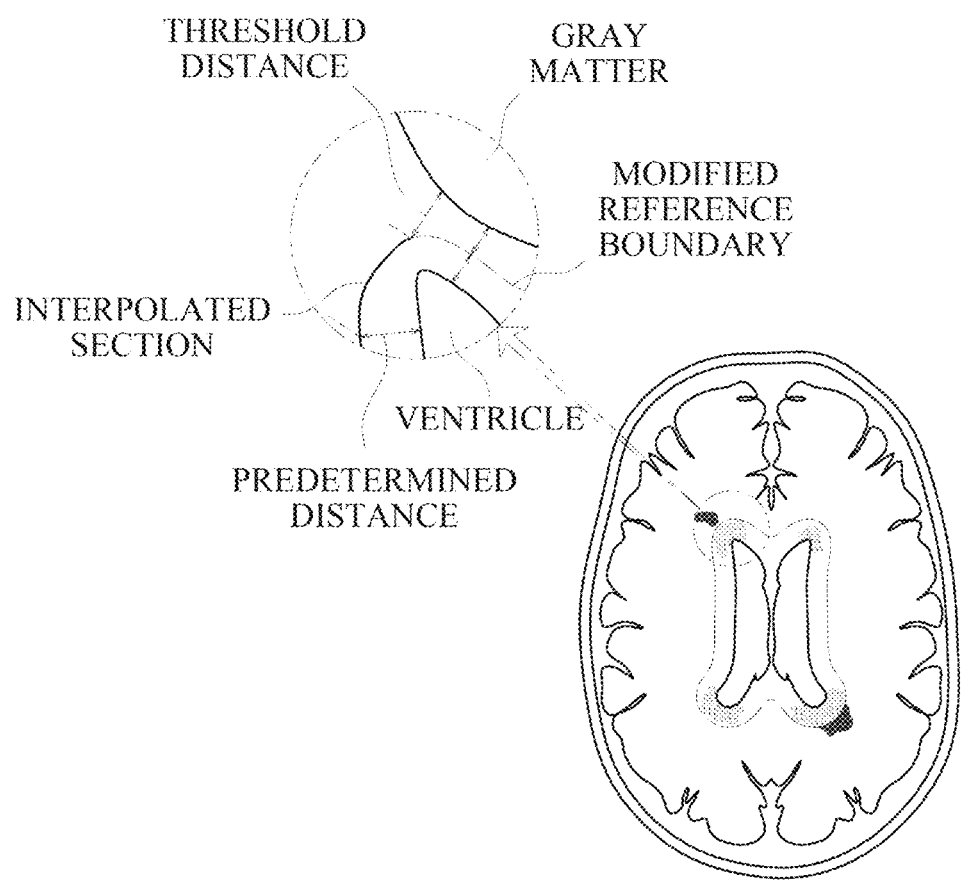
FIG. 19 illustrates an example of a modification process of a partially modified reference boundary according to an embodiment.

FIG. 19 illustrates an example of a modification process of a partially modified reference boundary according to an embodiment.

Referring to FIG. 19, the image analysis device 2000 may connect a modified reference boundary and an original reference boundary. Specifically, the second controller 2002 may determine a range to modification of a reference boundary in consideration of the distance between a reference region and a region of non-interest, and connect some regions of a modified reference boundary and the original reference boundary.

First, the second controller 2002 may modify the reference boundary from a first point at which the distance between the reference region and the region of non-interest is less than or equal to a threshold distance to a second point at which the distance between the reference region and the region of non-interest is less than or equal to the threshold distance. However, the above description is only an example, and a point at which the reference boundary and the region of non-interest overlap or a point at which the distance between the reference boundary and the region of non-interest is less than or equal to a predetermined distance may be selected as the first point. As a method of modifying the reference boundary, the method of any of the above-described embodiments or a method included within the idea of the present invention may be used.

Thereafter, the second controller 2002 may connect a first or second point, which is an end point of a modified region of the original reference boundary, and a third point at which the original reference boundary starts again. Here, the distance between the third point of the original reference region and a reference region may be predetermined as described above with reference to FIGS. 10 to 14.

The second controller 2002 may interpolate between a position value of the first or second point and a position value of the third point to connect the first or second point and the third point. Here, a length of an interpolation section between the second point and the third point may be variously set. For example, the interpolation section may be set in consideration of the distance between a region of non-interest and a region of interest.

A specific example will be described with reference to the drawing below.

The second controller 2002 may partially modify the reference boundary with respect to a section in which the distance between gray matter and a ventricle is small or the original reference boundary overlaps a gray matter region. The second controller 2002 may interpolate between a first point on a side of the modified reference boundary and a third point on the original reference boundary to connect the first point and the third point. Here, a point at which the distance between the gray matter and the ventricle is greater than or equal to a threshold distance may be selected as the second point. Alternatively, a point at which the distance between the modified reference boundary and the region of non-interest is greater than or equal to the threshold distance may be selected as the second point.

As such, the image analysis device 2000 according to an embodiment may set a reference boundary more accurately for calculation of a disease index by smoothly connecting the original reference boundary and the modified reference boundary, and the accuracy of the disease index obtained by the image analysis device 2000 may be improved due to the accurately set reference boundary.

When the disease index is calculated using the modified reference boundary, the image analysis device 2000 may provide diagnosis assistance information on the basis of the disease index obtained using the modified reference boundary. Specifically, the second controller 2002 may obtain a disease index as a result of analyzing a medical image using the modified reference boundary and provide diagnosis assistance information on the basis of the obtained disease index. Information about the provided disease index or disease information is similar to that described above with reference to FIG. 14, and thus a detailed description thereof will be omitted.

As described above, an accurate disease index may be obtained from more diverse images using the modified reference boundary than when a uniform reference boundary is used.

Although it is described above that the reference boundary is modified only when the reference boundary overlaps the gray matter region, a reference boundary may be set as described above with reference to FIGS. 15 to 19 and a method of appropriately setting a reference boundary as required at a field may be employed and used.

In the present specification, a method of analyzing a medical image has been mainly described above.

A method of providing diagnosis assistance information from a plurality of medical images when the plurality of medical images are analyzed by the image analysis device 2000 will be described below.

Figure 20:
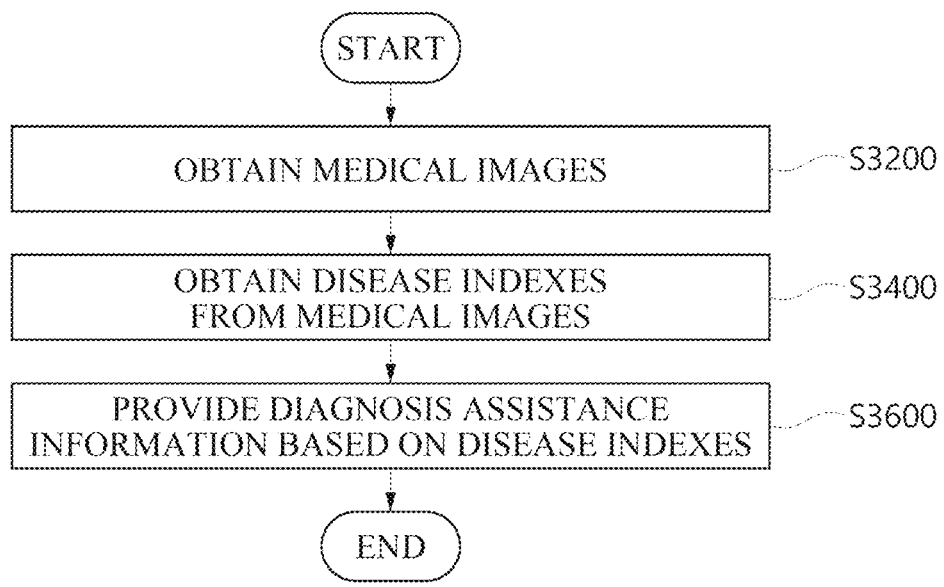
FIG. 20 is a schematic flowchart of a method of providing diagnosis assistance information from a plurality of medical images by an image analysis device according to an embodiment.

FIG. 20 is a schematic flowchart of a method of providing diagnosis assistance information from a plurality of medical images by the image analysis device 2000 according to an embodiment.

Referring to FIG. 20, a method of providing diagnosis assistance information from a plurality of medical images may include obtaining a plurality of medical images (S3200), obtaining disease indexes from the plurality of medical images (S3400), and providing diagnosis assistance information on the basis of the disease indexes (S3600).

First, the image analysis device 2000 may obtain a plurality of medical images (S3200). Specifically, the second controller 2002 may obtain a plurality of medical images from the image obtaining device 1000 through the second communication module 2800. Here, the plurality of medical images may be a set of tomographic images obtained by photographing an object. For example, the plurality of medical images may be a set of MRI slice images obtained by photographing an object.

Next, the image analysis device 2000 may obtain disease indexes from the plurality of medical images (S3400). Specifically, the second controller 2002 may obtain disease indexes from the plurality of medical images using a program for obtaining a disease index that is stored in the second memory 2400. Here, the second controller 2002 may obtain a disease index from each of the plurality of medical images or may obtain disease indexes from some of the plurality of medical images. A method of obtaining a disease index is as described above and thus a detailed description will be omitted.

When the plurality of disease indexes are obtained, the image analysis device 2000 may provide diagnosis assistance information on the basis of the disease indexes (S3600). Specifically, the second controller 2002 may obtain and provide diagnosis assistance information considering the disease indexes of the plurality of medical images. Here, the second controller 2002 may provide diagnosis assistance information for all or only some of the plurality of medical images from which disease indexes are calculated. A method of providing, by the image analysis device 2000, diagnosis assistance information for the plurality of medical images will be described in detail below.

An example of a plurality of medical images according to an embodiment and a method of providing diagnosis assistance information on the basis of the plurality of medical images will be described with reference to the drawings below.

Figure 21:
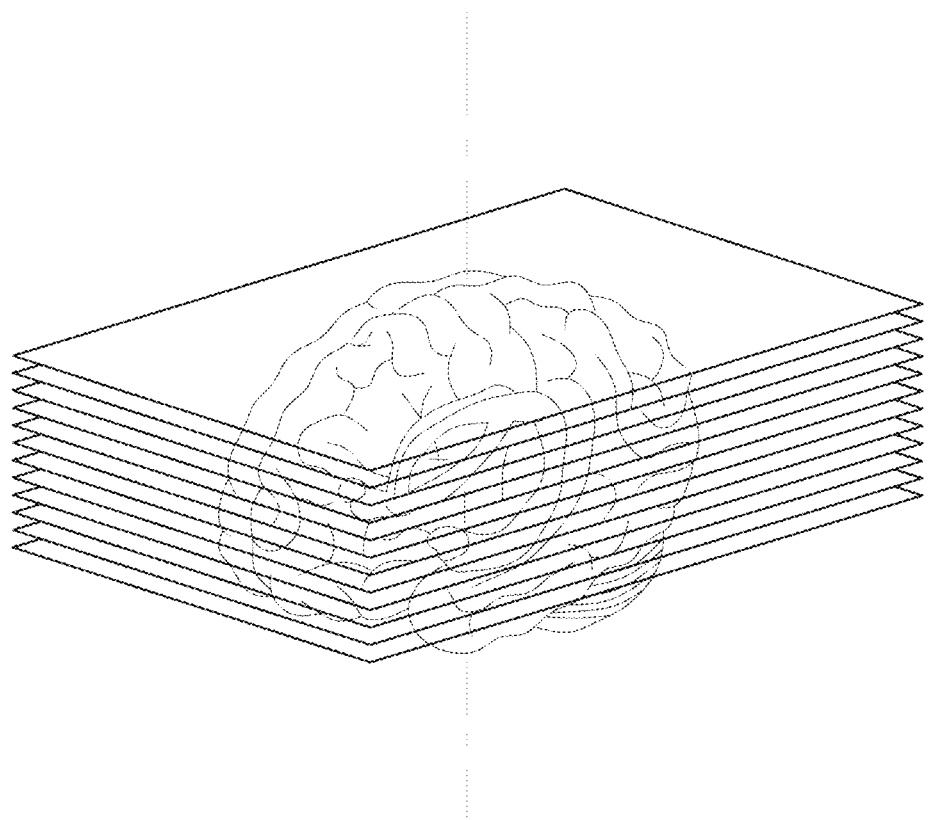
FIG. 21 illustrates an example of a plurality of medical images according to an embodiment.

FIG. 21 illustrates an example of a plurality of medical images according to an embodiment.

Referring to FIG. 21, the image analysis device 2000 may obtain a plurality of tomographic images related to an object. Specifically, the second controller 2002 may obtain a plurality of medical images, including a plurality of tomographic images of the object, through the second communication module 2800. Here, the plurality of tomographic images may include a set of sliced images as described above.

FIG. 21 illustrates an example of a plurality of medical images obtained by an MRI image device.

Referring to FIG. 21, the plurality of medical images include slice images related to a plurality of planes parallel to a first axis of the object. The sliced images may include information about the object photographed at positions spaced a certain distance from each other. That is, each the sliced image may include different information about the object. As such, the plurality of medical images may include information about multiple cross sections of the object and thus the image analysis device 2000 may analyze the plurality of medical images to obtain overall diagnosis assistance information about the object.

Figure 22:
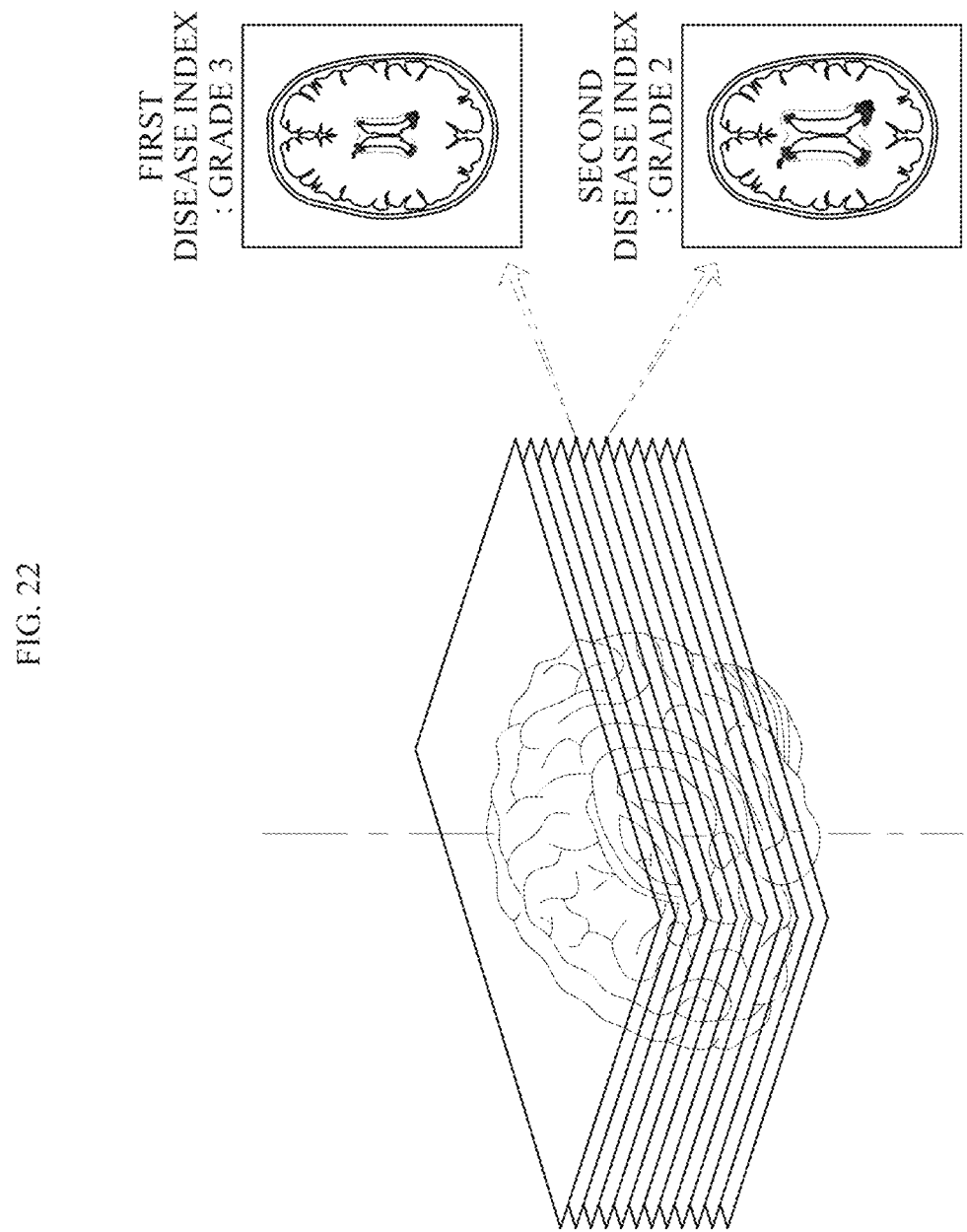
FIG. 22 illustrates an example of slice images containing different information and an example of providing diagnosis assistance information using the slice images.

FIG. 22 illustrates an example of slice images containing different information and an example of providing diagnosis assistance information using the slice images.

FIG. 22 illustrates an exemplary of a plurality of medical images obtained by photographing many cross sections of an object. Specifically, FIG. 22 shows a set of several slice images of an MRI image obtained by photographing a human brain.

FIG. 22A shows an MRI slice image related to a cross section of an upper side of the brain, and FIG. 22B shows an MRI slice image related to a cross section of a middle side of the brain.

FIG. 22A shows an image obtained by photographing a cross section of an upper region of the brain compared to FIG. 22B, in which a ventricle is shown to be smaller than that in FIG. 22B. In addition, in FIGS. 22A and 22B, a white matter region and a gray matter region are shown differently, and most importantly, different region information distinguished by WMH is included.

As described above, a disease index according to an embodiment may be obtained on the basis of the relationship between region information of a reference region and a target region. Therefore, different disease indexes may be calculated in the plurality of medical images including cross sections of the object at various positions. As a concrete example, a third-grade disease index is calculated in the case of FIG. 22A showing the cross section of the upper side of the brain and a second-grade disease index is calculated in the case of FIG. 22B showing the cross section of the middle side of the brain.

In this case, both diagnosis assistance information of FIG. 22A and diagnosis assistance information of FIG. 2B may be obtained, and the image analysis device 2000 may obtain and provide diagnosis assistance information of all or some of images.

That is, the image analysis device 2000 according to an embodiment may calculate disease indexes of a plurality of medical images obtained by photographing multiple cross sections of an object and provide diagnosis assistance information on the basis of the calculated disease indexes.

In addition, the image analysis device 2000 may provide diagnosis assistance information of all or some of the medical images for which disease indexes are calculated.

The image analysis device 2000 may select some of the medical image for which disease indexes are calculated and provide diagnosis assistance information for the selected medical images. Specifically, the second controller 2002 may select an image containing certain information from among the medical images for which diagnosis indexes are calculated, calculate a disease index of the selected image, and provide diagnosis assistance information.

Here, various criteria for selecting a medical image for which diagnosis assistance information is to be provided. That is, the image analysis device 2000 may select a medical image for which diagnosis assistance information is to be provided based on the type or grade of the disease index.

For example, the image analysis device 2000 may provide diagnosis assistance information of a medical image serving as a basis on which a grade of a disease index indicating a highest level of severity of the progress of a disease among the medical images for which disease indexes are calculated is calculated. As another example, the image analysis device 2000 may provide diagnosis assistance information of a medical image serving as a basis on which a grade of a disease index indicating a highest improvement rate of a state progress of the disease among the medical images, for which disease indexes are calculated, is calculated. As another example, the image analysis device 2000 may provide diagnosis assistance information of a medical image serving as a basis on which a grade of a disease index indicating an average value (or a median value) of disease indexes calculated from a plurality of medical images among the medical images, for which disease indexes are calculated, is calculated.

As another example, the image analysis device 2000 may provide diagnosis assistance information of a medical image for which a calculated first disease index is high, provide diagnosis assistance information of a medical image for which a calculated second disease index is high, or provide diagnosis assistance information from a combination of these medical images in consideration of the type of a disease index. In addition, the image analysis device 2000 may select a medical image for which diagnosis assistance information is to be provided in consideration of both the type and grade of a disease index.

Because calculated diagnosis assistance information may vary according to the type or grade of the disease index, the image analysis device 2000 may select a medical image, for which diagnosis assistance information is to be provided in consideration of the type or grade of a disease index, on the basis of a feature of an object (e.g., a patient), thereby providing diagnosis assistance information matching the patient.

In another embodiment, the image analysis device 2000 may select candidate images for calculation of a disease index from among a plurality of medical images and provide diagnosis assistance information on the basis of disease indexes obtained from the selected candidate images.

A method of providing diagnosis assistance information on the basis of disease indexes obtained by the image analysis device 2000 from candidate images will be described with reference to the drawings below.

Figure 23:
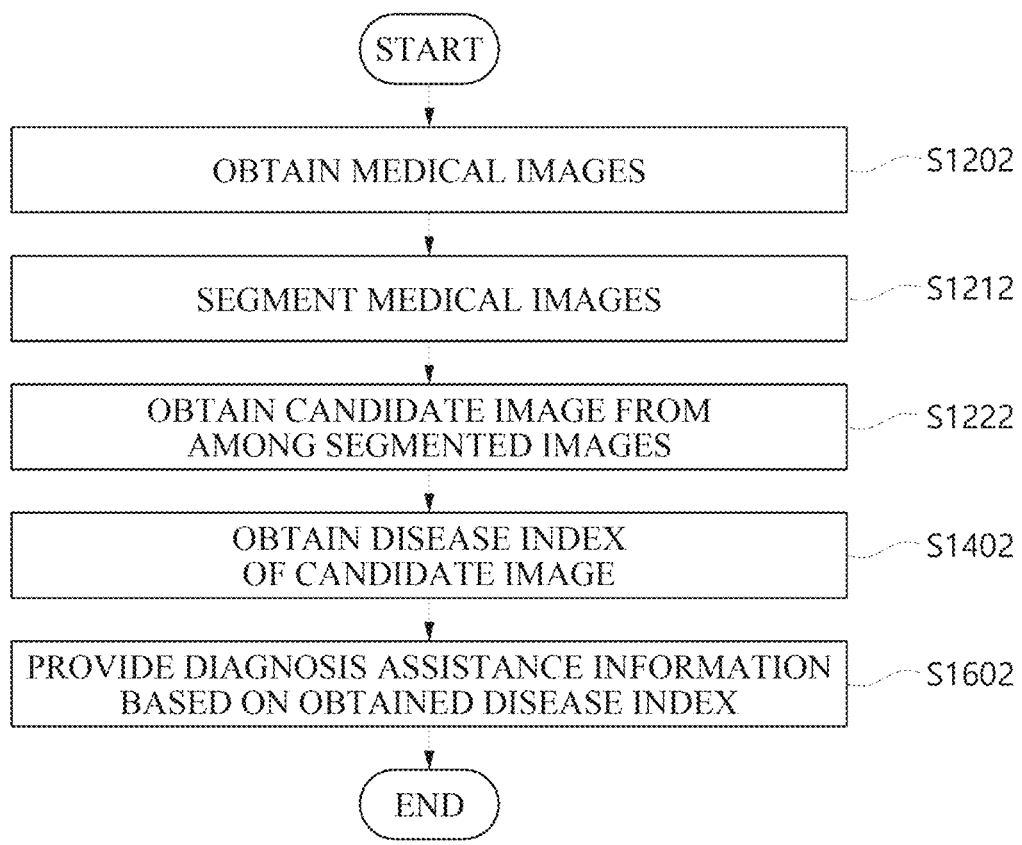
FIG. 23 is a schematic flowchart of a method of obtaining diagnosis assistance information from a candidate image according to an embodiment.

FIG. 23 is a schematic flowchart of a method of obtaining diagnosis assistance information from a candidate image according to an embodiment.

Referring to FIG. 23, a method of obtaining diagnosis assistance information from a candidate image by the image analysis device 2000 may include obtaining a plurality of medical images (S1202), segmenting the plurality of medical images (S1212), determining a candidate image from among the plurality of segmented images (S1222), obtaining a disease index of the selected candidate image (S1402), and providing diagnosis assistance information on the basis of the obtained disease index (S1602).

First, the image analysis device 2000 may obtain a plurality of medical images from the image obtaining device 1000 (S1202). The obtaining of the plurality of medical images (S1202) is as described above with reference to FIG. 20 and a detailed description is omitted here.

Thereafter, the image analysis device 2000 may segment the plurality of medical images (S1212). The segmenting of the plurality of medical images may be performed as described above and thus a detailed description is omitted here.

When the segmentation is performed, the image analysis device 2000 may determine candidate images from the plurality of segmented medical image (S1222). Specifically, the second controller 2002 may determine candidate images satisfying a predetermined criterion from among the plurality of segmented medical images in accordance with the predetermined criterion. The candidate images will be described in detail with reference to the drawings below.

When the candidate images are determined, the image analysis device 2000 may obtain disease indexes from the candidate image (S1402). Specifically, the second controller 2002 may obtain disease indexes with respect to all or some of the candidate images using a program for calculation of a disease index that is stored in the second memory 2002. A method of obtaining a disease index may be performed as described above and thus a detailed description is omitted here.

When the disease indexes are obtained, the image analysis device 2000 may obtain and provide diagnosis assistance information on the basis of the obtained disease indexes (S1602). Specifically, the second controller 2002 may provide diagnosis assistance information on the basis of disease indexes obtained from one or more candidate images. Here, as a method of providing diagnosis assistance information from the candidate images by the second controller 2002, a method of providing diagnosis assistance information from a plurality of medical images may be applied as described above with reference to FIGS. 20 to 22.

An example of extracting candidate images from a plurality of medical images and an example of calculating disease indexes from the extracted candidate images and providing diagnosis assistance information will be described with reference to the drawings below.

Figure 24:
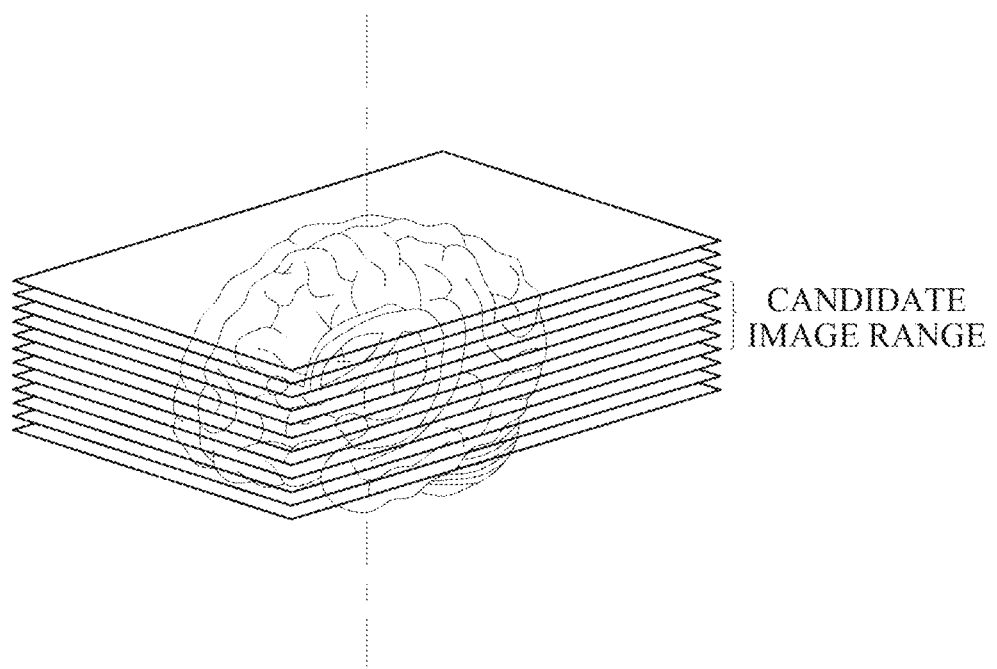
FIG. 24 illustrates an example of a candidate image according to an embodiment.

FIG. 24 illustrates an example of a candidate image according to an embodiment.

Referring to FIG. 24, the image analysis device 2000 may select a candidate image. Specifically, the second controller 2002 may select one or more candidate images from among a plurality of medical images obtained from the image obtaining device 1000. Here, the one or more candidate images may be images satisfying a predetermined criterion among the plurality of medical images.

Here, the predetermined criterion may be determined to correspond to a disease index to be calculated. For example, the predetermined criterion may be a criterion as to whether a reference region is included or not. That is, the second controller 2002 may select, as a candidate image, an image containing information about the reference region from among the plurality of medical images. As another example, the predetermined criterion may be a criterion as to whether a target region is included or not. That is, the second controller 2002 may select, as a candidate image, an image containing information about the target region from among the plurality of medical images. Alternatively, the second controller 2002 may select, as a candidate image, a medical image including both the target region and the reference region.

Here, the candidate image may be determined as one or more images included in a candidate image range as shown in the drawing. Here, the candidate image range may refer to a range from a first medical image satisfying a predetermined condition to a second medical image satisfying the predetermined condition from among tomographic images obtained consecutively by photographing the same object with respect to multiple planes on an axis. Here, the range from the first medical image to the second medical image may include a plurality of medical images positioned sequentially between the first medical image and the second medical image.

That is, specifically, referring to the drawing, when a reference region is a ventricle region, a candidate image range may be set to include a first medical image, which is a lowermost image, to a second medical image, which is an uppermost image, among medical images including the ventricular region among a plurality of medical images obtained by photographing transverse planes on a sagittal axis as consecutive cross sections.

In other words, the second controller 2002 may select candidate images or a candidate image range on the basis of whether the number of pixels corresponding to a predetermined condition included in each medical image is less than or equal to or greater than a threshold value.

Specifically, the second controller 2002 may analyze a segmentation result of a medical image to determine whether the number of pixels labeled as a ventricle is less than the threshold value. When the number of pixels labeled as a ventricle included in a medical image is equal to or greater than the threshold value, the second controller 2002 may determine the medical image as a candidate image.

When the second controller 2002 sets a candidate image range and a result of analyzing two adjacent medical images reveals that the number of pixels labeled as a ventricle included in one of the images is less than or equal to a threshold value and the number of pixels labeled as a ventricle included in the other image is equal to or greater than the threshold value, the other image may be set as a boundary of the candidate image range.

Figure 25:
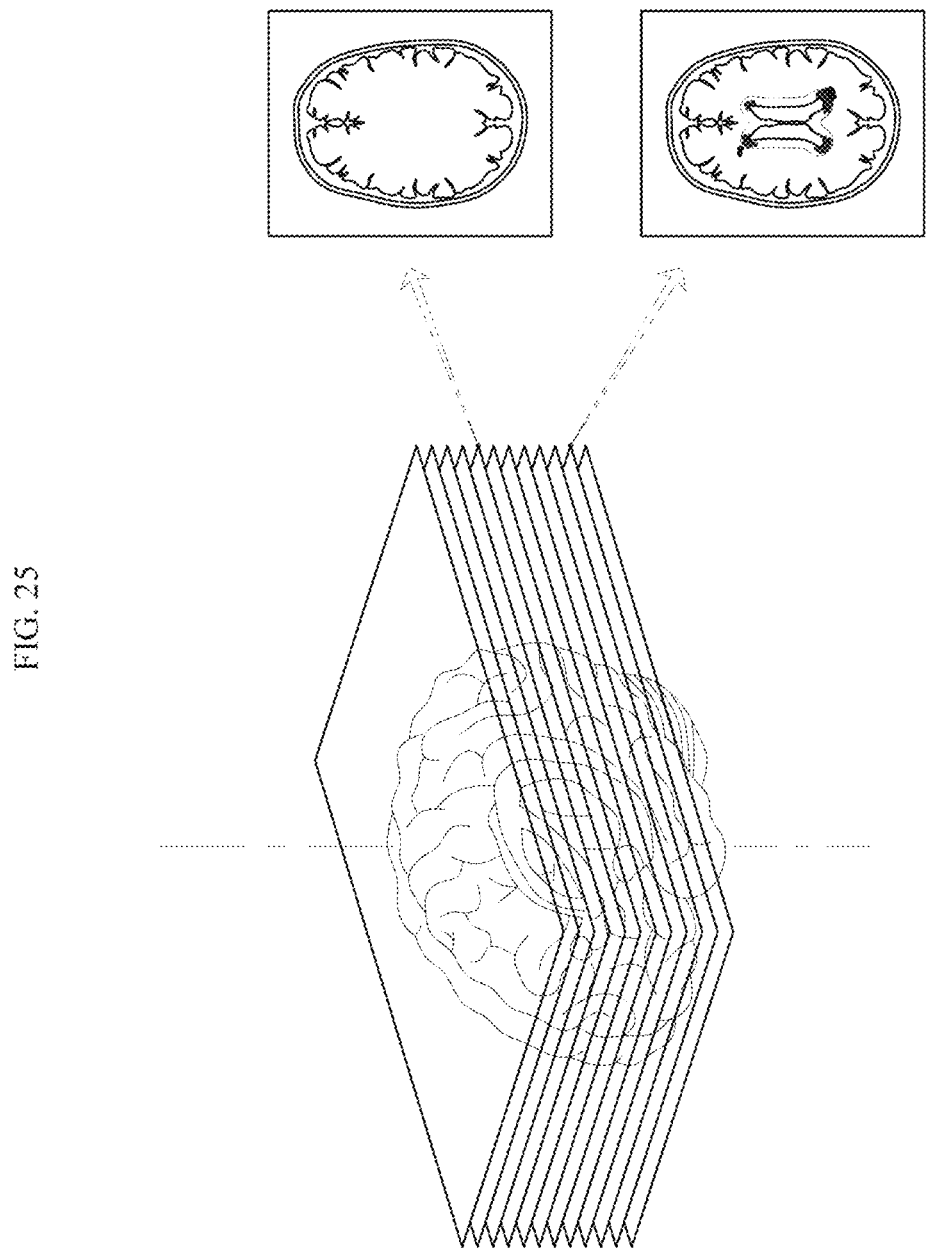
FIG. 25 illustrates an example of providing diagnosis assistance information from a candidate image according to an embodiment.

FIG. 25 illustrates an example of providing diagnosis assistance information from a candidate image according to an embodiment.

Referring to FIG. 25, the image analysis device 2000 may provide diagnosis assistance information from a candidate image. Specifically, the second controller 2002 may obtain a disease index from the candidate image and provide diagnosis assistance information on the basis of the obtained disease index.

A method of calculating a disease index is as described above and thus a detailed description will be omitted.

As illustrated in FIG. 25, FIG. 25A is a medical image other than a candidate image and FIG. 25B is a medical image determined as a candidate image.

According to an embodiment, it may be important to include a certain region of an object in a medical image when a disease index is calculated. For example, a method of obtaining a disease index according to an embodiment may be derived according to a correlation between a ventricle and WMH, and in this case, a disease index may be difficult to calculate and thus accurate diagnosis assistance information may not be provided when a ventricle is not included in a medical image. That is, FIG. 25A is a medical image that is obtained by photographing an upper end of the brain and does not include a ventricular region and thus a method of calculating a disease index according to an embodiment may be difficult to use therefor.

FIG. 25B is a medical image including a ventricular region and thus the second controller 2002 may be capable of analyzing the medical image in FIG. 25B to calculate a disease index and providing diagnosis assistance information on the basis of the calculated disease index.

When all medical images related to an object are analyzed, the amount of calculation of the image analysis device 2000 is excessive and thus the speed of calculation may be low, thereby causing an error during calculation.

However, in a method of providing diagnosis assistance information using a candidate image according to an embodiment, candidate images for which disease indexes are to be calculated are determined after segmentation of a plurality of images and thereafter disease indexes of only the determined candidate images are calculated to reduce the amount of calculation, thereby increasing the speed of calculation and improving the accuracy of calculation.

Figure 26:
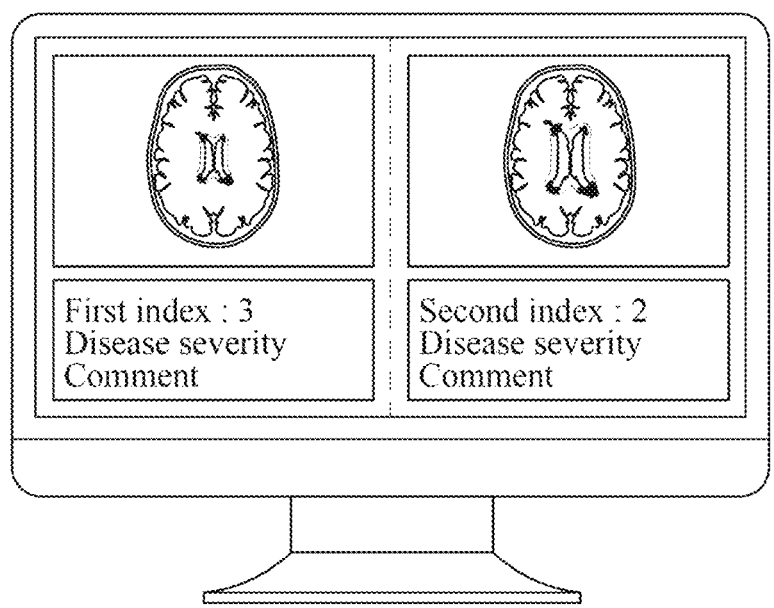
FIG. 26 illustrates another embodiment of providing diagnosis assistance information according to an embodiment.

FIG. 26 illustrates another embodiment of providing diagnosis assistance information according to an embodiment.

Referring to FIG. 26, the image analysis device 2000 according to an embodiment may provide diagnosis assistance information of at least one image among candidate images. Specifically, the second controller 2002 may provide diagnosis assistance information of at least one image satisfying a predetermined condition among medical images selected as candidate images.

Here, the predetermined condition may be set in consideration of a disease index. For example, the predetermined condition may be a disease index value indicating the progress of a most severe disease. That is, the second controller 2002 may select a certain medical image, in which a disease index represents the progress of a most severe disease among disease indexes of candidate images, as a medical image for providing diagnosis assistance information.

When a plurality of disease indexes may be calculated from the medical image, the predetermined condition may be determined in consideration of all of the plurality of disease indexes. That is, the second controller 2002 may select all of certain candidate images corresponding to the plurality of disease indexes as medical images for providing diagnosis assistance information or select only candidate images corresponding to some of the plurality of disease indexes as medical images for providing diagnosis assistance information.

Specifically, referring to the drawing, the second controller 2002 may provide diagnosis assistance information of a medical image satisfying a predetermined condition related to a first disease index among a plurality of medical images through the display module 2600. Here, the predetermined condition may be whether a grade of the first disease index of a plurality of candidate images is calculated to be the highest. In addition, through the display module 2600, the second controller 2002 may provide diagnosis assistance information of a medical image satisfying a predetermined condition related to a second disease index among a plurality of medical images and provide diagnosis assistance information of all medical images satisfying predetermined conditions related to the first disease index and the second disease index.

A method of determining a candidate image, which is for calculating a disease index, from among a plurality of medical images or a method of calculating a disease index of one medical image has been described above.

However, according to an embodiment, a disease index may be calculated using a plurality of medical images to calculate a disease index more accurately, as will be described with reference to FIGS. 27 to 29 below.

Figure 27:
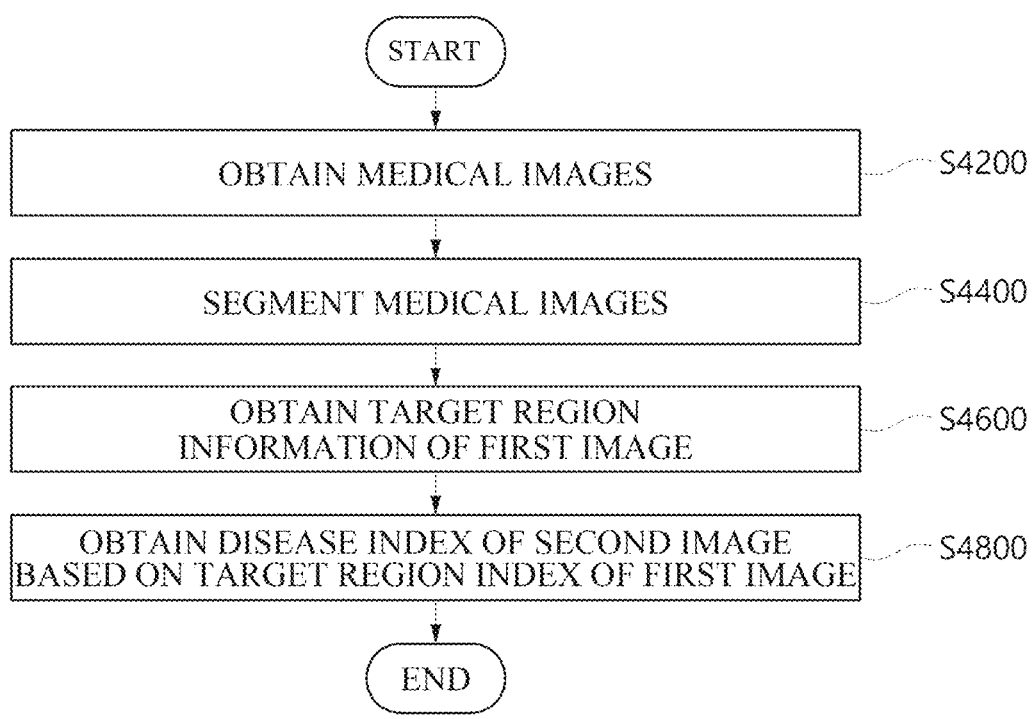
FIG. 27 is a flowchart of a method of obtaining a disease index on the basis of a plurality of images according to an embodiment.

FIG. 27 is a flowchart of a method of obtaining a disease index on the basis of a plurality of images according to an embodiment.

Referring to FIG. 27, a method of obtaining a disease index on the basis of a plurality of images according to an embodiment may include obtaining a plurality of medical images (S4200), segmenting the plurality of medical images (S4400), obtaining target region information of a first image (S4600), and obtaining a disease index of a second image on the basis of the target region index of the first image (S4800).

First, the obtaining of the plurality of medical images (S4200) and the segmenting of the plurality of medical images (S4400) may be performed as described above and thus a detailed description will be omitted.

After the plurality of medical images are segmented, the image analysis device 2000 may obtain information about a target region of a first image (S4600). Specifically, the second controller 2002 may obtain information about a target region corresponding to a disease index to be calculated. Here, the target region may refer to a region essential for calculation of a certain disease index. This will be described in detail below.

When the information about the target region is obtained, the image analysis device 2000 may calculate a disease index of the second image on the basis of the target region information of the first image. Specifically, the second controller 2002 may calculate a disease index related to the second image on the basis of the target region information obtained from the first image and region information related to an object included in the second image. Examples related thereto will be described below.

An example of a method of calculating a disease index of a second image on the basis of information about a first image will be described in detail with reference to the drawings below.

Figure 28:
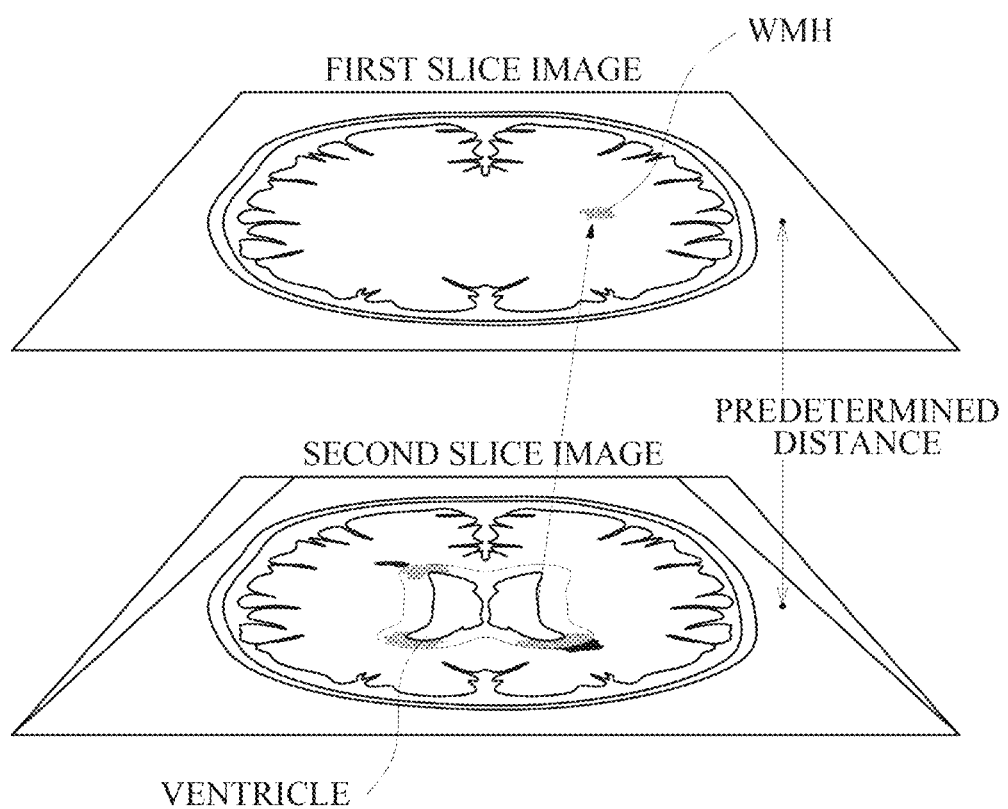
FIG. 28 illustrates an example of a process of calculating a disease index of a second image in consideration of information about a first image according to an embodiment.

FIG. 28 illustrates an example of a process of calculating a disease index of a second image in consideration of information about a first image according to an embodiment.

According to an embodiment, the image analysis device 2000 may calculate the disease index of the second image directly from the first image. Specifically, the second controller 2002 may calculate the disease index of the second image on the basis of the relationship between first region information included in the first image and second region information included in the second image. Here, the first region information may be information about a reference region included in the first image. The second region information may be information about a target region included in the second image.

In calculating a disease index, information about a reference region may not be included in a medical image but information about a target region may be included in the medical image. In this case, requirements for calculation of a disease index are not satisfied, and thus it may be difficult to calculate a disease index, but a disease index of such a medical image should be calculated in some cases.

That is, for example, referring to FIG. 28, a first slice image includes information about WMH but does not include information about a ventricle. In this case, a disease index derived from the relationship between the ventricle and the WMH may be difficult to derive from the first slice image. However, the WMH is likely to include significant information about the disease, and thus a disease index of an image including the WMH may be calculated to provide more accurate diagnosis assistance information.

In this case, the second controller 2002 may calculate the disease index of the second image in consideration of the information about the first image on the basis of the relationship between the first image and the second image. Here, the relationship between the first image and the second image may be obtained in advance. For example, the relationship between the first image and the second image may be the distance between slice images.

A specific example will be described with reference to the drawing below.

First, the second controller 2002 may determine a first image, which includes a target region for calculation of a disease index but does not include a reference region, as a result of segmenting a plurality of medical images. For example, according to an embodiment, although information about a ventricle and WMH is required to calculate a disease index, the second controller 2002 may select a first image that includes only the information about WMH but does not include the information about the ventricle in the medical image.

Thereafter, the second controller 2002 may select a second image, which includes a reference region that is not included in the first image, from among other medical images near the first image. Here, the second image may be an image immediately adjacent to the first image but is not limited thereto. For example, the second controller 2002 may select a second image including a ventricle for calculation of a disease index from among medical images (e.g., images spaced a certain distance or less from the first image on a sagittal axis) neighboring to the first image.

When the second image is selected, the second controller 2002 may calculate a disease index on the basis of the relationship between the reference region included in the second image and the target region included in the first image. For example, the second controller 2002 may calculate a disease index of the second image on the basis of information of the distance from a ventricular region included in the second image to WMH included in the first image and region information of WMH included in the second image. Here, the distance between the first image and the second image may be obtained and stored in advance.

Here, a criterion for deriving the relationship between the reference region included in the second image and the target region included in the first image may be variously determined. For example, the second controller 2002 may calculate a disease index on the basis of the distance from a center of the ventricular region included in the second image to a WMH region included in the first image. As another example, the second controller 2002 may calculate a disease index on the basis of the distance to the WMH region included in the first image from a ventricular region closest to the WMH region included in the first image among ventricle regions included in the second image. It will be understood by those of ordinary skill in the art that various methods using a criterion for calculation of the distance from the ventricular region included in the second image to the WMH region included in the first image are included in the technical idea of the present invention in addition to the method described above as an example.

A method of calculating a disease index of a second image indirectly from a first image will be described with reference to the drawings below.

Figure 29:
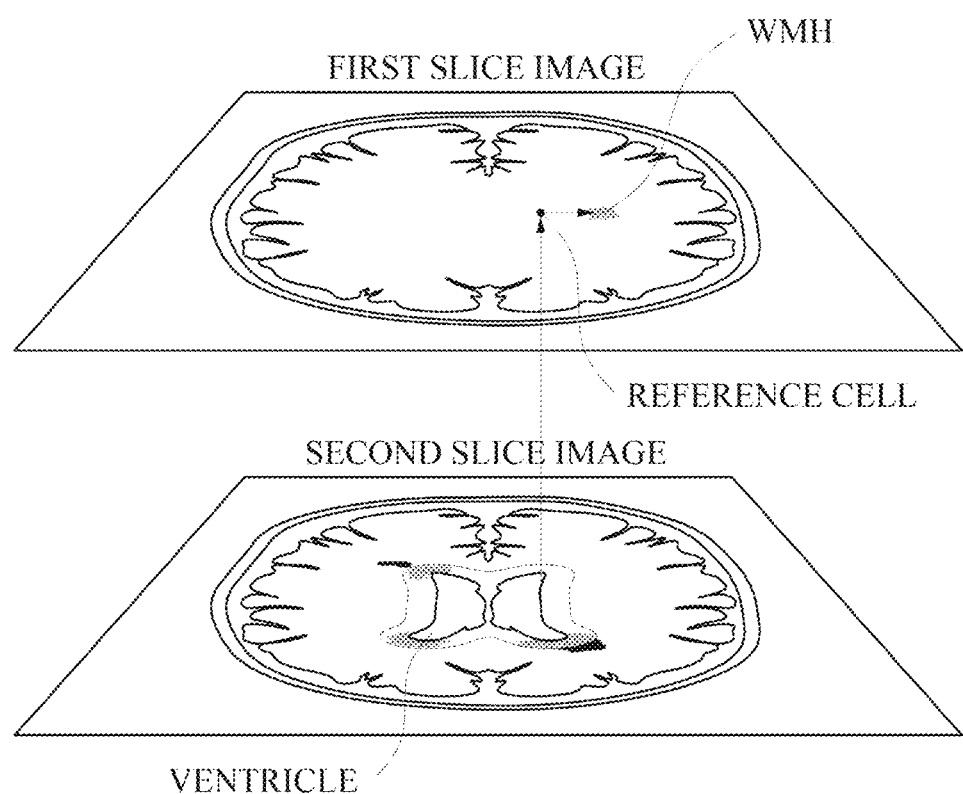
FIG. 29 illustrates another example of a process of calculating a disease index of a second image in consideration of information about a first image according to an embodiment.

FIG. 29 illustrates another example of a process of calculating a disease index of a second image in consideration of information about a first image according to an embodiment.

According to an embodiment, the image analysis device 2000 may calculate the disease index of the second image directly from a first image. Specifically, the second controller 2002 calculates the disease index of the second image on the basis of the relationship between a reference cell included in the second image obtained indirectly from information about a reference region included in the first image and a target region included in the second image.

A specific example will be described with reference to the drawing below.

As described above with reference to FIG. 27, the second controller 2002 may determine a first image, which includes a target region for calculation of a disease index but does not include a reference region in the medical image, as a result of segmenting a plurality of medical images.

For example, according to an embodiment, although information about a ventricle and WMH is required to calculate a disease index, the second controller 2002 may select a first image that includes only information about WMH but does not include information about a ventricle in the medical image.

Thereafter, the second controller 2002 may select a second image, which includes a reference region that is not included in the first image, from among other medical images near the first image. For example, the second controller 2002 may select a second image including a ventricular region for calculation of a disease index from among medical images near the first image.

When the second image is selected, the second controller 2002 may determine a reference cell in the first image corresponding to a reference region included in the second image on the basis of information about the reference region included in the second image. For example, the second controller 2002 may determine a reference cell in the first image corresponding to a ventricular region included in the second image on the basis of information about the ventricular region included in the second image.

When the reference cell is determined, the second controller 2002 may calculate a disease index on the basis of information about the reference cell and the target region included in the first image. That is, for example, the second controller 2002 may regard a reference cell, as ventricular, in a second region corresponding to a ventricular region included in the first image and derive the relationship between the reference cell and WMH included in the first image to calculate a disease index. A method of calculating a disease index as described above may be used as a method of calculating a disease index on the basis of the relationship between the reference cell and the WMH.

As described above, according to an embodiment, the image analysis device 2000 may calculate a disease index using a plurality of medical images to obtain an accurate disease index and provide diagnosis assistance information on the basis of the disease index.

In addition, the diagnosis assistance information providing system 10000 according to an embodiment may calculate a disease index through a 3D medical model obtained by 3D modeling a medical image and provide diagnosis assistance information.

A method of providing diagnosis assistance information on the basis of a 3D medical model will be described with reference to FIGS. 30 to 32 below.

Figure 30:
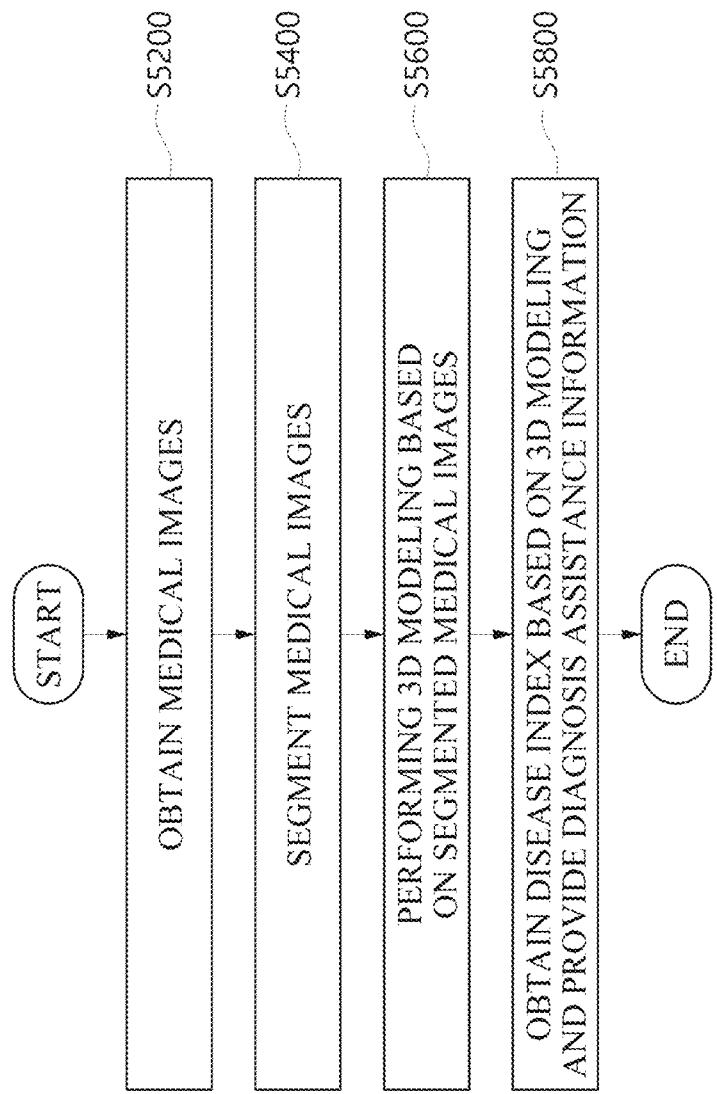
FIG. 30 is a flowchart of an example of a method of providing diagnosis assistance information on the basis of a three-dimensional (3D) medical model according to an embodiment.

FIG. 30 is a flowchart of an example of a method of providing diagnosis assistance information on the basis of a 3D medical model according to an embodiment.

According to an embodiment, a method of providing diagnosis assistance information on the basis of a 3D medical model, which is performed by the image analysis device 2000, may include obtaining a plurality of medical images (S5200), segmenting the plurality of medical images (S5400), performing 3D modeling on the basis of the segmented medical images (S5600), and obtaining a disease index on the basis of the 3D modeling (S5800).

The obtaining of the plurality of medical images (S5200) and the segmenting of the plurality of medical images (S5400) may be performed as described above and thus a detailed description will be omitted.

When the plurality of medical images are segmented, the image analysis device 2000 may obtain a 3D medical model on the basis of the plurality of segmented medical images (S5600). Specifically, the second controller 2002 may generate a 3D medical model by processing a plurality of medical images obtained by consecutively photographing cross sections of an object. Here, the 3D medical model may be generated based on the plurality of segmented medical images and may include 3D pixel information reflecting information about a plurality of brain regions. That is, the plurality of brain regions may be segmented in three dimensions. In addition, a reference boundary as described above may be formed in three dimensions.

When the 3D medical model is obtained, the image analysis device 2000 may obtain a disease index on the basis of the 3D medical model and provide diagnosis assistance information. Specifically, the second controller 2002 may calculate a disease index from the 3D medical model using a program for obtaining a disease index that is stored in the second memory 2400 and obtain diagnosis assistance information from the calculated disease index.

An example of calculating a disease index from a 3D medical model and providing diagnosis assistance information will be described with reference to the drawings below.

Figure 31:
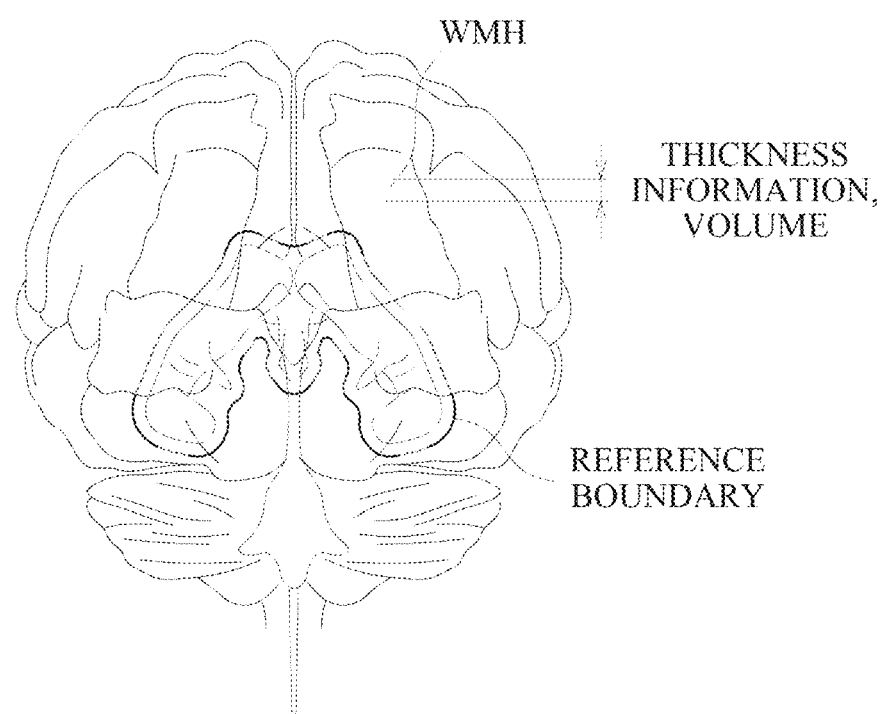
FIG. 31 illustrates an example of a process of calculating a disease index from a 3D medical image according to an embodiment.

FIG. 31 illustrates an example of a process of calculating a disease index from a 3D medical model according to an embodiment. FIG. 32 illustrates another example of a process of calculating a disease index according to an embodiment.

Referring to FIG. 31, the image analysis device 2000 may obtain a disease index on the basis of region information included in a 3D medical model. Specifically, the second controller 2002 may calculate a disease index on the basis of information about one or more certain regions of an object included in the 3D medical model. Here, the one or more certain regions may include a target region and a reference region as described above. Specifically, the one or more certain regions may include a cell (e.g., a voxel) labeled as a target region or a reference region expressed in three dimensions. Here, the second controller 2002 may set a criterion for deriving the relationship between one or more regions included in an object.

For example, the second controller 2002 may calculate a disease index on the basis of information about a ventricular region and a WMH region that are included in the 3D medical model. Here, the second controller 2002 may set a reference boundary to derive the relationship between the ventricular region and the WMH region as described above. That is, the second controller 2002 may set a set of cells spaced a predetermined distance from a 3D ventricle region as a reference boundary. Similar to the reference boundary set in the medical image described above, the second controller 2002 may set or modify a reference boundary in various ways.

The second controller 2002 may calculate a disease index in consideration of the relationship with the WMH region on the basis of the reference boundary formed in three dimensions. Here, the relationship between the reference boundary and the WMH is as described above. As 3D modeling is performed on a two-dimensional medical image, information about regions of an object, e.g., region information of a target region, may be 3D physical quantity. That is, the second controller 2002 may obtain 3D information, e.g., a thickness of a certain region included in the object, which cannot be obtained from the 2D medical image, through 3D modeling. As another example, the information about the WMH may be volume (or a value) corresponding to cells tagged as the WMH.

Figure 32:
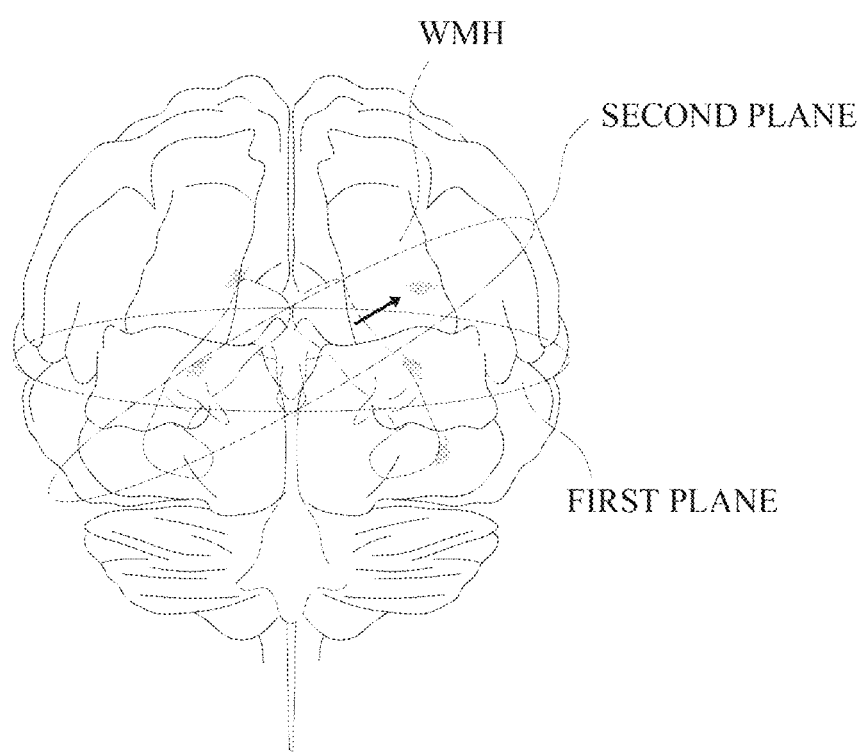
FIG. 32 illustrates another example of a process of calculating a disease index from a 3D medical image according to an embodiment.

Referring to FIG. 32, the image analysis device 2000 may calculate a disease index on the basis of a plurality of planes included in a 3D medical model and provide diagnosis assistance information. Specifically, the second controller 2002 may calculate a disease index on the basis of at least one plane of the 3D medical model including information about at least one certain region related to an object, and provide diagnosis assistance information.

As the 3D modeling is performed, the relationship between certain regions for calculation of the disease index may be easily derived. That is, when a disease index is calculated by analyzing a slice image, the disease index may not be easy to obtain and the accuracy of the disease index may be low when the slice image does not include information about an essential region for calculation of a disease index that is included in an object.

However, when a disease index is calculated by performing 3D modeling, a plane may be determined to include all regions necessary for calculation of a disease index and a disease index may be calculated with respect to the plane, thereby improving the accuracy of the disease index.

A specific example will be described with reference to the drawing below.

Referring back to FIG. 32, the second controller 2002 may set a first plane to correspond to a predetermined criterion so that both a ventricular region and a first WMH region may be included in the first plane and calculate a disease index with respect to the first plane. Here, various criteria may be used to set the first plane. For example, the first plane may be a plane set in consideration of the distance between a target region and a reference region. More specifically, the first plane may be a plane set to include a straight line at which the distance between the WMH region and the ventricular region is minimal.

As another example, the second controller 2002 may set a second plane in consideration of the number of target regions included in the plane and calculate a disease index with respect to the set second plane. For example, the second controller 2002 may set the second plane to include a largest number of target regions in addition to the information about the reference region. Alternatively, the second controller 2002 may set a second plane such that a maximum number of pixels may be labeled as the target region.

That is, the second controller 2002 may set a first plane to include a first target region and the reference region and a second plane to include a second target region and the reference region according to various criteria. In this case, the first plane and the second plane may form a certain angle together. As such, the image analysis device 2000 may also derive the relationship between a reference region and a target region, calculate a disease index, or provide diagnosis assistance information with respect to a plane forming a certain angle with a plane including a medical image which is a base of a 3D medical model.

Examples of a method of obtaining a disease index from one or more medical images and providing diagnosis assistance information on the basis of the disease index, the method being performed by the diagnosis assistance information providing system 10000, according to various embodiments have been described above.

As described above, in a method of providing diagnosis assistance information, performed by the diagnosis assistance information providing system 10000, according to an embodiment, a disease index may be calculated from a medical image on the basis of an algorithm or a program automated according to a clear and uniform criterion so that the disease index may be calculated more objectively while excluding a human subjective judgment, thereby providing more accurate diagnosis assistance information.

A method of segmenting certain regions included in a medical image by the diagnosis assistance information providing system 10000 according to an embodiment will be described below.

According to an embodiment, the diagnosis assistance information providing system 10000 may segment a medical image. Specifically, the image analysis device 2000 may obtain a medical image from the image obtaining device 1000 and segment the obtained medical image. More specifically, the second controller 2002 may segment the medical image using the algorithm for image segmentation that is stored in the second memory 2400.

This will be described with reference to the drawings below.

Figure 33:
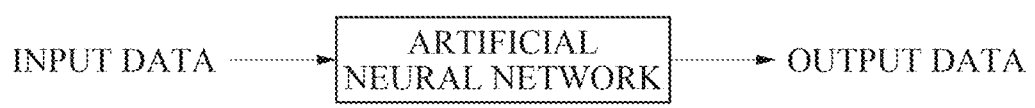
FIG. 33 illustrates an outline of a segmentation operation of a medical image, performed by an image analysis device, according to an embodiment.

FIG. 33 illustrates an outline of a segmentation operation of a medical image that is performed by an image analysis device according to an embodiment.

According to an embodiment, the image analysis device 2000 may receive input data and output data. Specifically, the second controller 2002 may input a medical image obtained from the image obtaining device 1000 as input data to an algorithm for image segmentation so as to obtain output data including a segmentation result of the medical image.

The image analysis device 2000 according to an embodiment may use various algorithms for image segmentation.

For example, a machine learning model may be provided as the algorithm for image segmentation. A representative example of the machine learning model may include an artificial neural network. Specifically, a representative example of the artificial neural network includes a deep learning artificial neural network that includes an input layer for receiving data, an output layer for outputting a result, and a hidden layer interposed between the input layer and the output layer to process data.

Specifically, examples of the artificial neural network include a convolution neural network, a recurrent neural network, a deep neural network, etc., and the artificial neural network should be understood, as used herein, to include the artificial neural network described above, other various types of artificial neural networks, and a combination thereof and are not necessarily limited to the deep learning artificial neural network.

In addition, the machine learning model is not necessarily limited to the artificial neural network model and may further include the K-nearest neighboring algorithm (KNN), RandomForest, the support vector machine (SVM), and the principal component analysis (PCA), etc. and may include an ensemble thereof or a combination of other various methods. It should be understood in embodiments described with respect to an artificial neural network that the artificial neural network may be replaced with other machine learning models unless otherwise specified.

Furthermore, as used herein, an algorithm for image segmentation is not necessarily limited to the machine learning model. That is, the algorithm for image segmentation may include various judgment/determination algorithms other than the machine learning model.

Therefore, as used herein, the algorithm for image segmentation should be understood in a comprehensive sense to include various types of algorithms for analyzing a medical image and identifying regions included in the medical image.

An example of an artificial neural network model will be described with reference to FIGS. 34 and 35 below.

Figure 34:
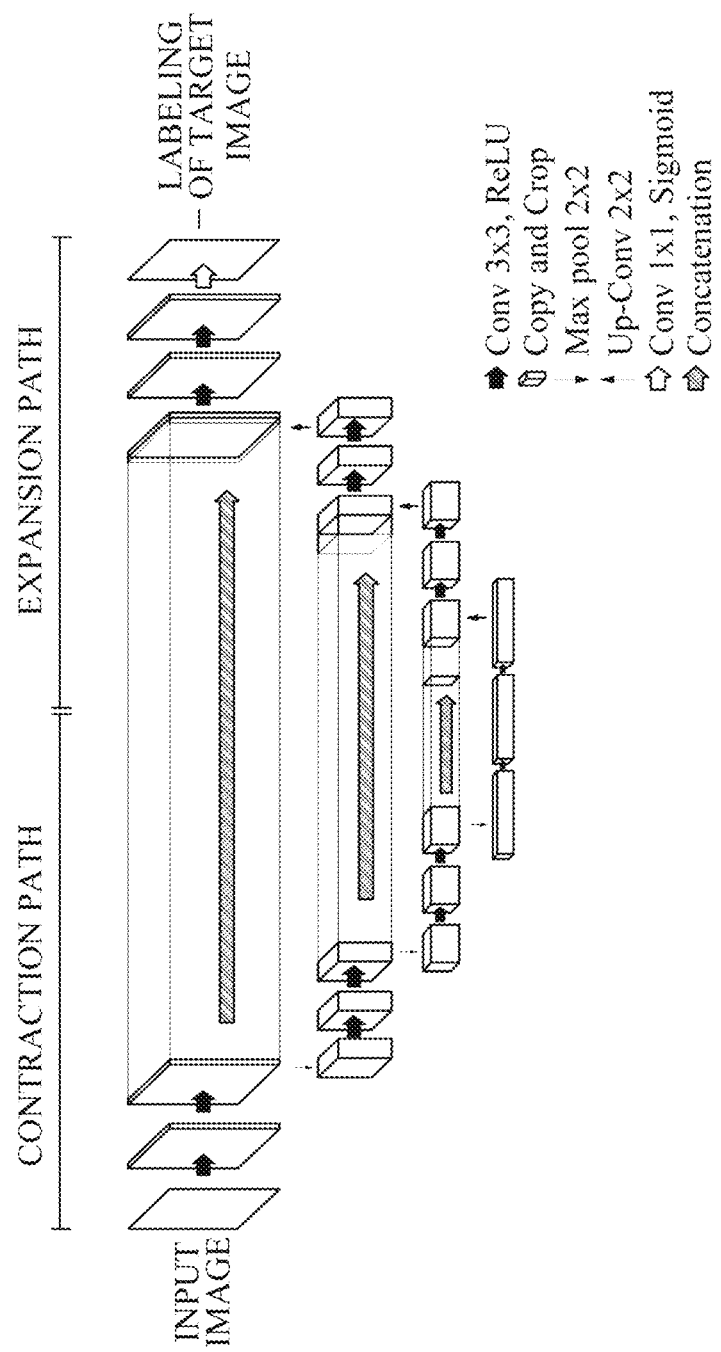
FIG. 34 illustrates an example of an artificial neural network model according to an embodiment.

FIG. 34 illustrates an example of an artificial neural network model according to an embodiment.

Referring to FIG. 34, the image analysis device 2000 according to an embodiment of the present invention may use a U-net as an artificial neural network for image segmentation.

The U-net generally used for image segmentation may be configured as an architecture including a contraction path and an expansion path.

Specifically, the contraction path of the U-net can be configured such that two-times convolution and max pooling are consecutively performed. In this case, in the contraction path of the U-net, features related to an image may be extracted.

However, because the size of a feature map reduces in the contraction path, the U-net may further include the expansion path to restore the size of the feature map.

The expansion path of the U-net may be configured such that up-convolution and two-times convolution are consecutively performed. In this case, in the expansion path of the U-NET, the image and the size of the feature map may be extracted.

In addition, an architecture of the U-net may be configured for concatenation of feature maps of the same level to provide location information related to characteristics to the expansion path from the contraction path.

In this case, based on the difference between a label of an input image and a label of an output segmentation map, at least one parameter or weight of at least one node of a layer included in the U-net may be adjusted such that the difference between the label of the input image and the label of the target segmentation map is minimal.

Figure 35:
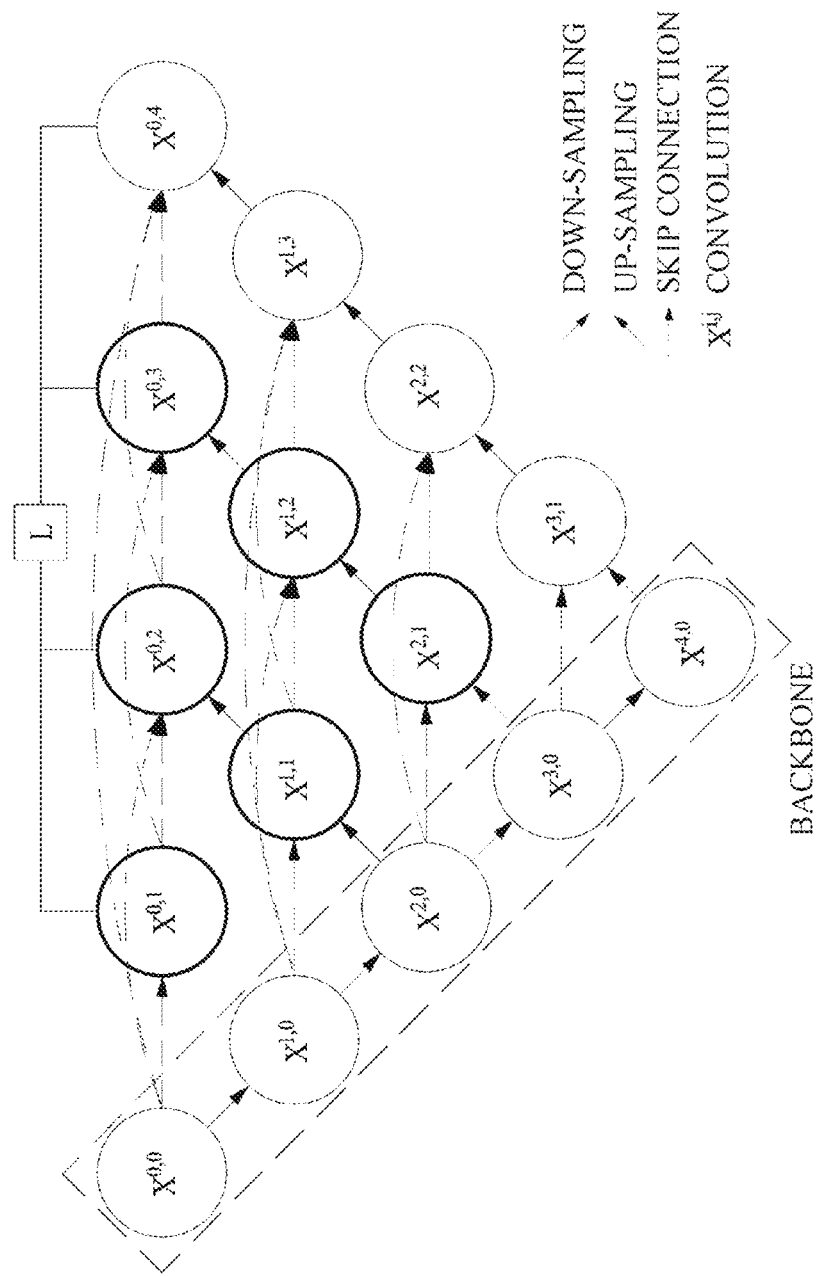
FIG. 35 illustrates another example of an artificial neural network model according to an embodiment.

FIG. 35 illustrates another example of an artificial neural network model according to an embodiment.

Referring to FIG. 35, the image analysis device 2000 according to an embodiment may use a U-net++ as an artificial neural network for image segmentation. The U-net++ is an artificial neural network model using the high-density block idea of DenseNet to improve the performance of the U-net and is different from the U-net in that in a skip path, there is a convolutional layer to connect a semantic gap between an encoder and a decoder feature map and there is a dense skip connection to improve a gradient flow.

Specifically, the image analysis device 2000 may be implemented to input an input image to an input layer of a U-net++neural network model and obtain label information output from an output layer thereof. In this case, the image analysis device 2000 may adjust a parameter or weight of at least one node of a hidden layer included in the U-net++ on the basis of the difference between label information included in the input image and the label information output from the neural network model.

More specifically, the second controller 2002 may be implemented to repeatedly adjust the parameter or weight of the at least one node so as to obtain a parameter or weight of the at least one node for minimizing the difference between the label data included in the input image and the label data output from the neural network model.

FIG. 36 illustrates an example of a segmentation result using an artificial neural network according to an embodiment.

According to an embodiment, the image analysis device 2000 may segment a medical image based on a feature of the medical image. Specifically, the second controller 2002 may segment the medical image to correspond to a condition under which the medical image is obtained.

Here, the condition under which the medical image is obtained may vary according to a configuration parameter of the image obtaining device 1000. For example, the condition under which the medical image is obtained may be a predetermined magnetic condition parameter value of the image obtaining device 1000. Specifically, when the image obtaining device 1000 is implemented as an MRI device, a T1-weighted image or a T2-weighted image may be obtained according to a TR/TE value, and the second controller 2002 may segment an image to correspond to the obtained image. Here, the feature of the medical image according to the condition under which the medical image is obtained is as described above.

A specific example will be described with reference to the drawing below.

FIG. 36 illustrates a result of segmenting a T1-weighted image and a T2-FLAIR image of the same object.

According to an embodiment, the second controller 2002 may segment the T1-weighted image. Here, the T1-weighted image may be segmented to identify an anatomical feature. As shown in the drawing, the result of segmenting the T1-weighted image reveals that a wrinkled portion of an outer gray matter region is more clearly segmented than in the result of segmenting the T2-FLAIR image.

According to an embodiment, the second controller 2002 may segment the T2-FLAIR image. Here, the T2-FLAIR image may be segmented to determine a lesion feature. As shown in the drawing, the result of segmenting the T2-FLAIR image further includes information about a WMH region as compared to the result of segmenting the T1-weighted image.

Therefore, even when a medical image is obtained by photographing the same object, features (e.g., an anatomical feature and a lesion feature) included in the medical image may vary according to a condition under which the image obtaining device 1000 is obtained, and information that may be observed in the medical image may vary according to the features of the medical image.

However, more accurate diagnosis assistance information may be provided if necessary when all of features of multiple medical images are considered. Therefore, in the following description, a process of segmenting a medical image to include a plurality of features will be described.

Figure 37:
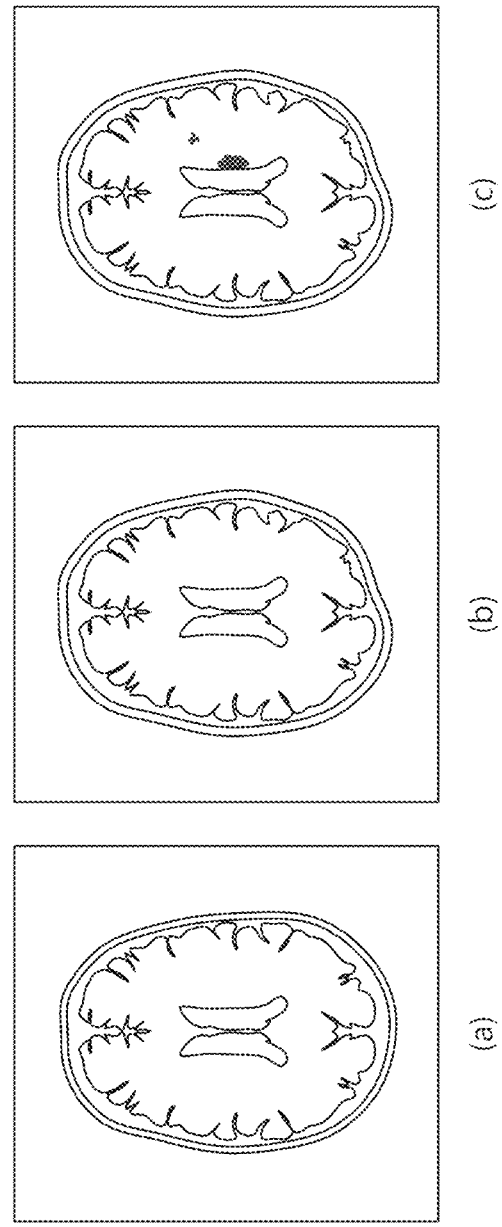
FIG. 37 illustrates an example of a medical image segmented to include a plurality of features according to an embodiment.

FIG. 37 illustrates an example of a medical image segmented to include a plurality of features according to an embodiment.

Referring to FIG. 37, the image analysis device 2000 according to an embodiment may segment a medical image to include at least two features that may vary according to an image acquisition condition. Specifically, the second controller 2002 may segment a first image to include a feature of a second image on the basis of the first image.

A specific example will be described with reference to the drawing below.

The second controller 2002 may input a first medical image having a first feature as input data to an artificial neural network to obtain output data labeled with the first feature and a second feature related to a second medical image. Here, the artificial neural network may be trained on the basis of a learning set related to the second image having the second feature. For example, the first feature may be an anatomical or structural feature and thus the first image may be a T1-weighted image. The second feature may be a lesion feature and thus the second image may be a T2-FLAIR image.

More specifically, as shown in FIG. 37A, the second controller 2002 may input a first image having a lesion feature (e.g., a T2-FLAIR image) as input data to an artificial neural network according to an embodiment.

Here, when the artificial neural network trained only with a learning set related to the first image is used, the second controller 2002 outputs only a segmentation result including only the first feature (i.e., the lesion feature) as shown in FIG. 37B.

However, the artificial neural network according to an embodiment may be trained using a learning set based on both the first image related to the first feature and the second image relating to the second feature. Thus, the second controller 2002 may input the first image to the artificial neural network to obtain a segmentation result of the first image reflecting both the first feature and the second feature as shown in FIG. 37C.

As described above, even when a medical image including one feature is segmented, information about a plurality of features may be obtained to obtain information about various diseases from one medical image and thus the image analysis device 2000 according to an embodiment may provide more accurate and diverse diagnosis assistance information from the medical image.

A training process of an artificial neural network according to an embodiment will be described with reference to the drawings below.

Figure 38:
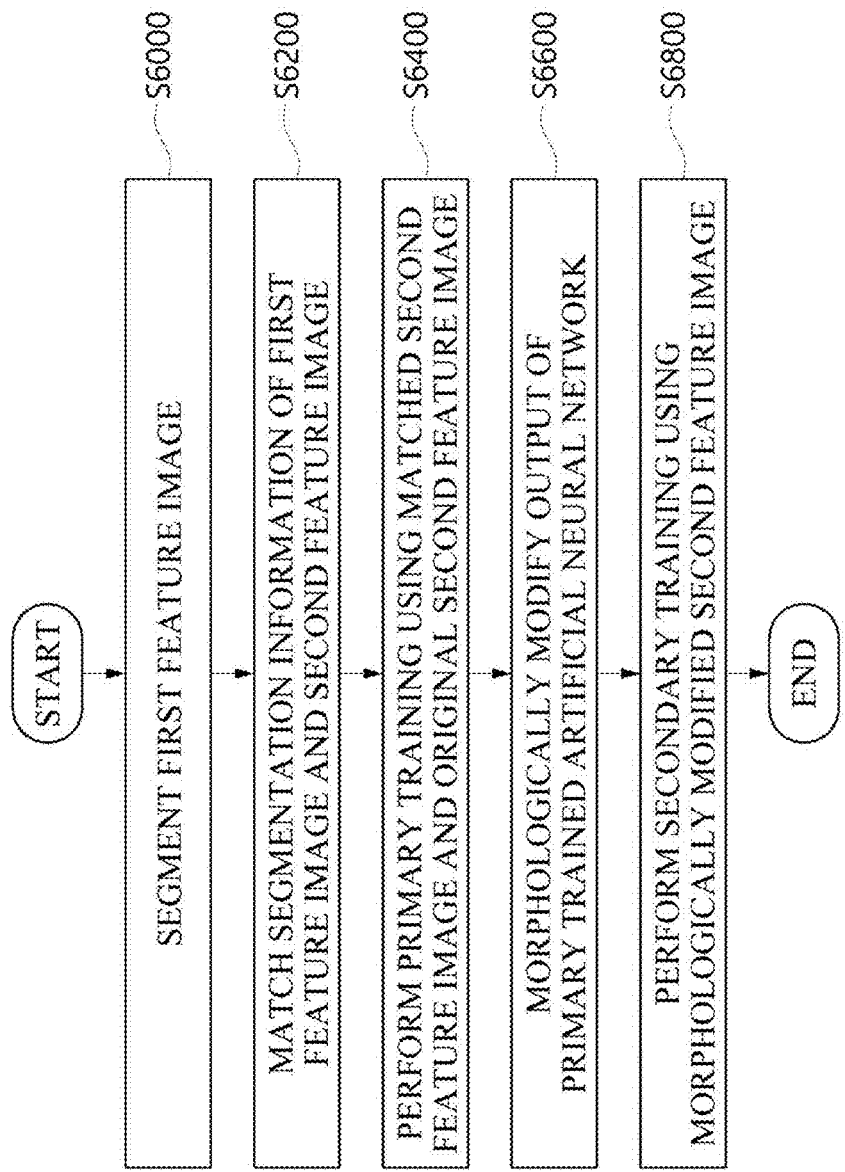
FIG. 38 is a flowchart illustrating a training process of an artificial neural network according to an embodiment.

FIG. 38 is a flowchart illustrating a training process of an artificial neural network according to an embodiment.

An artificial neural network according to an embodiment may be trained using training data. Here, the artificial neural network according to an embodiment may be trained through a variety of devices capable of driving an artificial neural network algorithm. For example, the artificial neural network may be trained through the image analysis device 2000. In the present specification, the artificial neural network according to an embodiment will be described as being trained through the image analysis device 2000 but is not limited thereto and may be trained through another device for driving an artificial neural network.

Figure 39:
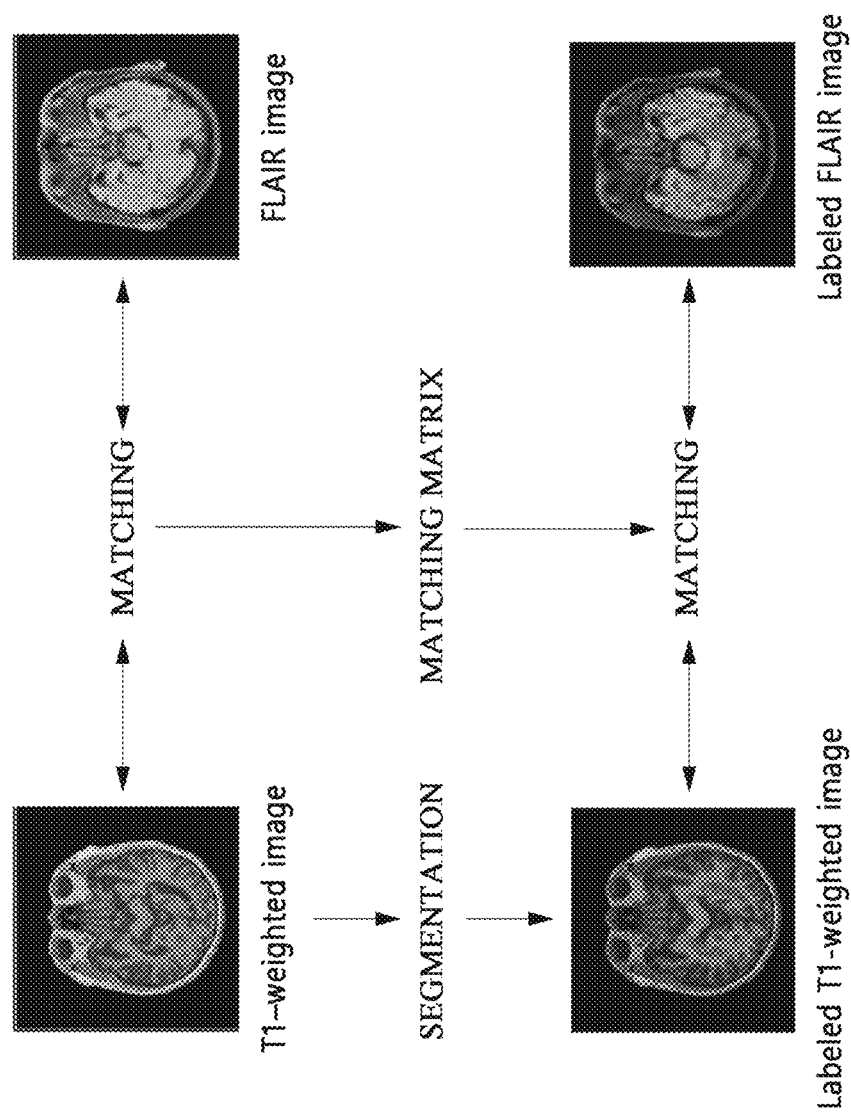
FIG. 39 illustrates an example of a matching process of a first image and a second image according to an embodiment.

Referring to FIG. 39, the training process of the artificial neural network according to an embodiment may include segmenting a first image having a first feature (S6000), matching segmentation information of the first image on the basis of a second image having a second feature (S6200), performing primary training using a matched image and the second image (S6400), morphologically modifying the second image including an output of the primary training (S6600), and performing secondary training using the second image including a morphologically modified segmentation result (S6800).

First, the image analysis device 2000 may segment the first image having the first feature (S6000). Specifically, the second controller 2002 may segment the first image to include information about a first feature obtained under a first acquisition condition. In other words, the image obtaining device 1000 may segment the first image having a first feature obtained when a first parameter is set.

After the first image is segmented, the image analysis device 2000 may match the segmented first image and the second image on the basis of the second image (S6200). Specifically, the second controller 2002 may obtain the second image to include segmented information about the first feature by matching the first image, which is segmented to include the first feature, to the second image having the second feature. In other words, the first image segmented to include the first feature may be matched to the second image having the second feature obtained when a second parameter of the image obtaining device 1000 is set. This will be described in detail below.

After the first image and the second image are matched, the image analysis device 2000 may perform primary training using the matched second image and the second image that is not matched (S6400). Specifically, the second controller 2002 may train the artificial neural network according to an embodiment using the second image and the result of matching the second image to reflect the first feature so that the artificial neural network may output a segmentation result including the first feature from the second image.

That is, the artificial neural network according to an embodiment may be trained using a learning set including the second image labeled with the first feature and the original second image. Therefore, the artificial neural network may receive the second image as input data and output the second image labeled with the first feature. Although the learning set is described herein as including the original second image, not only the original second image, but also a result of processing the original second image may be used. For example, the second image may refer to a second image segmented to include the second feature. Alternatively, the second image may refer to a second image on which another preprocessing process is performed. However, for convenience of description, training the artificial neural network using a learning set based on the original second image will be described below.

After the primary training of the artificial neural network, the image analysis device 2000 may perform morphological modification on an output image of the primarily trained artificial neural network (S6600). Specifically, the second controller 2002 may perform morphological modification on the second image, which is segmented to include a second feature output when original second image data is input to the artificial neural network, so as to increase the accuracy of a segmentation result.

The primarily trained artificial neural network may not include accurate information about the first feature. Therefore, the image analysis device 2000 according to an embodiment may morphologically modify primary output data of the artificial neural network on the basis of the first image including the first feature to improve the accuracy of calculation of the artificial neural network so that the artificial neural network may identify information about the first feature on the second image more accurately.

When the morphological modification of the primary output data of the artificial neural network is completed, the image analysis device 2000 may secondarily train the artificial neural network on the basis of the morphologically modified second image (S6800). Specifically, the second controller 2002 may train the artificial neural network according to an embodiment on the basis of a learning set including the second image morphologically modified and labeled with the first feature. That is, the artificial neural network according to an embodiment may be trained using the learning set including the second image labeled to reflect the morphologically modified first feature and thus may perform segmentation to reflect information about the first feature from the second image.

An example of a training process of an artificial neural network according to an embodiment will be described with reference to the drawings below.

FIG. 39 illustrates an example of a matching process of a first image and a second image according to an embodiment.

Referring to FIG. 39, the image analysis device 2000 according to an embodiment may match a first image and a second image. Specifically, the second controller 2002 may obtain a matching matrix between the first image and the second image. Here, the matching matrix may refer to a conversion function between the first image and the second image. That is, the matching matrix according to an embodiment may refer to a function representing a correlation between a first point included in a first image and a second point included in a second image of the same object. Here, the first point and the second point may refer to pixels or a set of pixels.

The image analysis device 2000 according to an embodiment may process the second image to correspond to a segmentation result of the first image using the matching matrix on the basis of the first image segmented with respect to a first feature. That is, the second controller 2002 may segment the second image to reflect the segmentation result of the first image with respect to the first feature into the second image. Here, the second image may be segmented in advance to include a second feature as described above. That is, the second controller 2002 may segment the second image to reflect both the first feature and the second feature.

More specifically, the first image may be a T1-weighted image, and the second image may be a T2-FLAIR image. That is, first, the image analysis device 2000 may obtain the matching matrix by matching the T1-weighted image and the T2-FLAIR image.

In addition, the image analysis device 2000 may segment the T1-weighted image to reflect an anatomical or structural feature of the T1-weighted image. For example, the second controller 2002 may process the T1-weighted image so that a certain region of the brain may be distinguishable. For example, the second controller 2002 may segment the T1-weighted image such that organs included in the brain, e.g., cerebrum, cerebellum, diencephalon, and hippocampus, parts of the brain, e.g., temporal lobe, frontal lobe, and occipital lobe, or a combination thereof may be distinguished from one another.

Thereafter, the image analysis device 2000 may match the segmented T1-weighted image with the T2-FLAIR image using the matching matrix so that the segmentation result of the T1-weighted image may be reflected in the T2-FLAIR image.

Accordingly, the image analysis device 2000 may obtain the T2-FLAIR image segmented to reflect the anatomical feature. Specifically, the second controller 2002 may segment the T2-FLAIR image, in which WMH or substances of the brain, such as white matter, gray matter, etc., observed in a medical image are distinguished from one another, to reflect the anatomical feature. The T2-FLAIR image segmented to reflect the anatomical feature may be used to primarily train the artificial neural network as described above.

Figure 40:
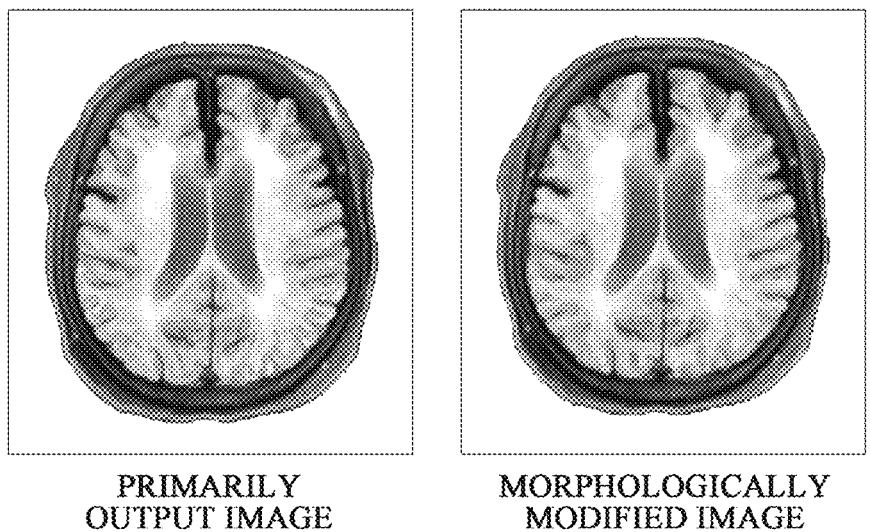
FIG. 40 illustrates an example of a morphological modification according to an embodiment.

FIG. 40 illustrates an example of a morphological modification according to an embodiment.

Referring to FIG. 40, the image analysis device 2000 according to an embodiment may morphologically modify a segmentation result of a medical image. Specifically, the second controller 2002 may morphologically modify a segmentation result reflecting a first feature included in a second image. The second image including the morphologically modified segmentation result may reflect the first feature more accurately.

A specific example will be described with reference to the drawing below.

As described above, the artificial neural network may be trained primarily using the T2-FLAIR image segmented to reflect the anatomical feature and an original T2-FLAIR image. The artificial neural network may receive the T2-FLAIR image and output, as a result of the primary training, the T2-FLAIR image segmented to reflect a feature (anatomical or structural feature) of the T1-weighted image. The segmented T2-FLAIR image, which is an output of the artificial neural network, is the T2-FLAIR image segmented to reflect the feature of the T1-weighted image but may be incomplete in some regions thereof and thus may need to be modified.

FIG. 40A is a result of primarily training an artificial neural network according to an embodiment, in which an outer portion of a segmented section reflects anatomical features incompletely. In contrast, FIG. 40B is a morphologically modified primary output of the artificial neural network in which an outer portion of a segmented section reflects the anatomical features accurately.

More specifically, in FIG. 40A, some gray matter regions are not distinguishable and a boundary line of each region is partially broken. In addition, noise labeled with incorrect regions is included due to incomplete training.

However, in the morphologically modified medical image, gray matter regions are distinguishable and certain regions are clearly distinguished by boundary lines thereof.

Here, according to an embodiment, the second controller 2002 may perform morphological modification on the basis of a structural feature of the brain. In general, the regions of the brain, including the ventricle, should be connected in 26 ways in three dimensions. Thus, the second controller 2002 may reduce noise included in a segmented medical image on the basis of a correlation between the regions of the brain.

Here, the ventricle may be erroneously distinguished from other non-tissues and thus may be mislabeled as non-tissue. In this case, in order to compensate for false labeling of a ventricular region, the second controller 2002 may label the ventricular region using a fill-hole method.

As described above, the artificial neural network according to an embodiment may be re-trained by inputting thereto a result of morphologically modifying a segmentation result and thus may output a result to more accurately reflect a feature to be included.

Figure 41:
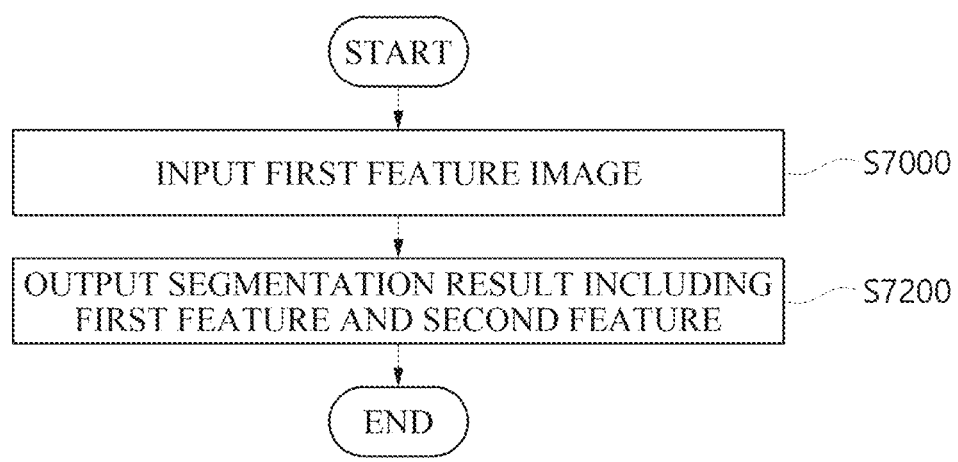
FIG. 41 is a flowchart of a deploying process performed using an artificial neural network by an image analysis device according to an embodiment.

FIG. 41 is a flowchart of a deploying process performed using an artificial neural network by an image analysis device according to an embodiment.

Referring to FIG. 41, the deploying process performed according to an embodiment using an artificial neural network by the image analysis device 2000 may include inputting a first image having a first feature (S7000) and outputting the first image processed to include a segmentation result including the first feature and a second feature (S7200).

First, the image analysis device 2000 may input the first image having the first feature to the artificial neural network (S6000). Specifically, the second controller 2002 may input the first image having the first feature to an artificial neural network trained thoroughly and stored in the second memory 2400. Here, the artificial neural network has been trained thoroughly through the above-described training process.

When the first image is input, the image analysis device 2000 may obtain the first image processed to include the first feature related to the first image and a second feature related to a second image that is in a form different than that of the first image as an output t of the artificial neural network (S7200). Specifically, the second controller 2002 may obtain the first image segmented such that the first feature related to the first image and the second feature related to the second image different from the first image may be distinguished from each other in a comprehensive manner.

Thus, by using an artificial neural network thoroughly trained through the training process of an artificial neural network according to an embodiment, the image analysis device 2000 may obtain a medical image segmented to include both a first feature and a second feature different from the first feature even when a medical image having only the first feature is input to the artificial neural network. Therefore, various pieces of information necessary to analyze a disease so as to obtain information related to the disease may be obtained and analyzed to provide various pieces of information about the disease to a user.

Figure 42:
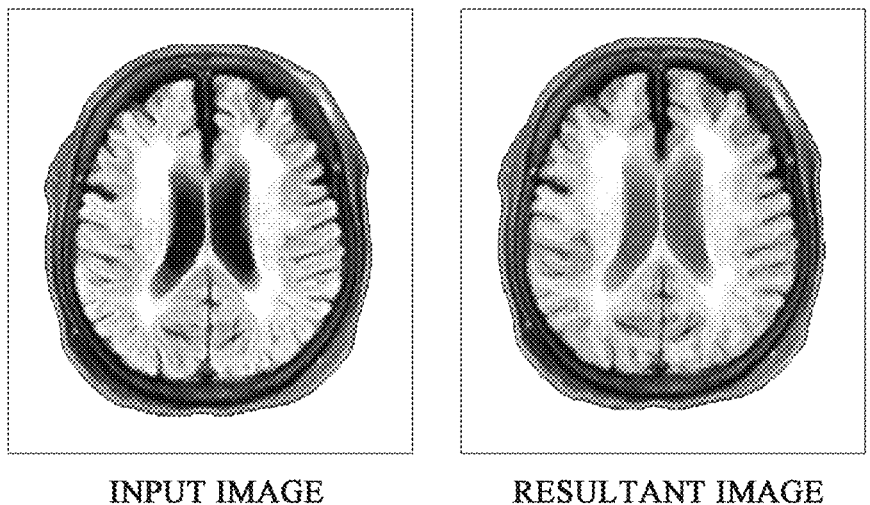
FIG. 42 illustrates an example of a final output of an artificial neural network according to an embodiment.

FIG. 42 illustrates an example of a final output of an artificial neural network according to an embodiment.

Referring to FIG. 42, the image analysis device 2000 may input a first image to an artificial neural network so as to obtain a first image processed to include various features. Specifically, the second controller 2002 may input a first image reflecting a first feature to the artificial neural network so as to obtain the first image segmented to further reflect a feature different from the first feature.

Specifically, referring to the drawing, the image analysis device 2000 may input a T2-FLAIR image to the artificial neural network to obtain an image processed to reflect a feature of a T1-weighted image.

Specifically, the second controller 2002 may input the T2-FLAIR image to an artificial neural network trained thoroughly on the basis of a learning set reflecting the feature of the T1-weighted image and a feature of the T2-FLAIR image so as to obtain the T2-FLAIR image segmented to accurately reflect the feature of the T1-weighted image. Here, the artificial neural network may be trained to segment the T2-FLAIR image to reflect an original feature of the T2-FLAIR image. That is, when the T2-FLAIR image is input as input data to the artificial neural network according to an embodiment, an image segmented to reflect an anatomical or structural feature easily observed from the T1-weighted image and to include all lesion features easily observed in the T2-FLAIR image may be obtained.

More specifically, a final output of the artificial neural network according to an embodiment may be based on the T2-FLAIR image in which a lesion feature such as WMH and substances, e.g., white matter and gray matter, of the brain are distinguishable and may be segmented to include all features of the T1-weighted image, e.g., the organs included in the brain and parts of the brain.

Methods according to embodiments may be embodied as program instructions executable through various computer means and recorded on a computer-readable recording medium. The computer-readable recording medium may include program instructions, data files, data structures, etc. solely or in combination. The program instructions recorded on the medium may be specially designed and configured for embodiments or may be known to those skilled in computer software. Examples of the computer-readable recording medium include magnetic media, e.g., a hard disk, a floppy disk, and magnetic tape, optical media, e.g., CD-ROM and DVD, magneto-optical media, e.g., a floptical disk, and hardware devices, e.g., ROM, RAM, and flash memory, which are specially configured to store and execute program instructions. Examples of the program instructions include not only machine language code created by a compiler but also high-level language code executable by a computer using an interpreter or the like. A hardware device as described above may be configured to operate as one or more software modules to perform operations of an embodiment and vice versa.

Although embodiments have been described above in conjunction with the limited number of embodiments and the drawings, various modifications and changes may be made to the above description by those of ordinary skill in the art. For example, an appropriate result may be achieved even when the above-described techniques are performed in an order different from that described herein and/or the above-described components such as a system, a structure, a device, and a circuit, are combined in a form different from that described herein or replaced with other components.

Therefore, other implementations, other embodiments, and equivalents to the claims are also within the scope of the claims described below.

The invention claimed is:

1. A method for providing a diagnostic auxiliary information, the method comprising:
   obtaining a plurality of brain-related images;
   selecting one or more candidate images including information related to the ventricle region and the white matter hyperintensity (WMH) region among the plurality of images;
   obtaining a disease index from the candidate images; and
   selecting a target medical image corresponding to a disease index satisfying a predetermined condition among the plurality of disease indexes by considering the plurality of disease indexes calculated from the candidate images,
   wherein the selecting one or more candidate images includes segmenting the brain-related images to obtain information on a plurality of brain regions in the images, detecting the brain regions corresponding to the ventricle region and the white matter hyperintensity region, and determining the image including both the ventricle region and the white matter hyperintensity region among the plurality of images as the candidate images,
   wherein the obtaining the disease index includes determining at least one of a width or area of a white matter hyperintensity region included in the candidate image, determining a distance between the ventricle region and the white matter hyperintensity region, and calculating the disease index by considering the width or area of the white matter hyperintensity region and the distance between the ventricle region and the white matter hyperintensity region, and
   wherein the target medical image corresponding to the disease index satisfying the predetermined condition is a medical image indicating the highest grade value of disease index.

2. The method of claim 1, the method further comprising:
   outputting diagnostic auxiliary information related to the target medical image,
   wherein the diagnostic auxiliary information is obtained from the disease index calculated from the target medical image.

3. The method of the claim 1,
   wherein the disease index includes a first disease index and a second disease index.

4. The method of the claim 3,
   wherein the target medical image corresponding to the disease index satisfying the predetermined condition is a medical image in which any one of the first disease index and the second disease index indicates the highest grade value of the disease index.

5. The method of the claim 3,
   wherein the target medical image corresponding to the disease index satisfying the predetermined condition is a medical image with the highest grade value of both the first disease index and the second disease index.

6. The method of the claim 3,
   wherein the disease index further includes a third disease index and the third disease index is obtained in consideration of the first disease index and the second disease index.

7. The method of the claim 6,
   wherein the target medical image corresponding to the disease index satisfying the predetermined condition is a medical image with the highest grade value of the third disease index.

8. The method of the claim 1,
   wherein the target medical image corresponding to the disease index satisfying the predetermined condition is a medical image in which the width or area of the white matter hyperintensity region is measured to be the largest.

9. The method of the claim 8, the method further comprising:
   outputting the diagnostic auxiliary information obtained from the target medical image; and
   wherein the diagnostic auxiliary information includes a width or area of the white matter hyperintensity region.

10. A device for providing a diagnostic auxiliary information, the device comprising:
    a communication module for obtaining a plurality of medical images;
    a controller for analyzing the medical images; and
    a display module for outputting analysis results for the plurality of medical images;
    wherein the controller selects one or more candidate images containing information related to both the ventricle and white matter hyperintensity (WMH) among the plurality of medical images,
    the controller determines region information of the white matter hyperintensity region included in the candidate image, determines a distance between the ventricle and the white matter hyperintensity region, and calculates a disease index in consideration of region information of the white matter hyperintensity region and the distance between the ventricle and the white matter hyperintensity region to obtain disease index from the candidate images, and
    the controller selects a target medical image corresponding to a disease index satisfying a predetermined condition among the plurality of disease indexes in consideration of a plurality of disease indexes calculated from the candidate images, and outputs diagnostic auxiliary information obtained from the disease index through the display module, and
    wherein the target medical image corresponding to the disease index satisfying the predetermined condition is a medical image indicating the highest grade value of disease index.

11. A computer-readable electronic recording medium storing computer program for executing the method of claim 1.

12. The device of the claim 10,
    wherein the disease index includes a first disease index and a second disease index.

13. The device of the claim 12,
    wherein the target medical image corresponding to the disease index satisfying the predetermined condition is a medical image in which any one of the first disease index and the second disease index indicates the highest grade value of the disease index.

14. The device of the claim 12,
    wherein the target medical image corresponding to the disease index satisfying the predetermined condition is a medical image with the highest grade value of both the first disease index and the second disease index.

15. The device of the claim 12,
wherein the disease index further includes a third disease index and the third disease index is obtained in consideration of the first disease index and the second disease index.

16. The device of the claim 15,
wherein the target medical image corresponding to the disease index satisfying the predetermined condition is a medical image with the highest grade value of the third disease index.

17. The device of the claim 10,
wherein the target medical image corresponding to the disease index satisfying the predetermined condition is a medical image in which the width or area of the white matter hyperintensity region is measured to be the largest.

18. The device of the claim 17,
wherein the controller outputs the diagnostic auxiliary information obtained from the target medical image, and
wherein the diagnostic auxiliary information includes a width or area of the white matter hyperintensity region.

* * * * *